(12) United States Patent
Eaves

(10) Patent No.: US 11,298,133 B2
(45) Date of Patent: Apr. 12, 2022

(54) FORCE MODULATING TISSUE BRIDGE

(71) Applicant: EMRGE, LLC, Atlanta, GA (US)

(72) Inventor: Felmont Eaves, Altanta, GA (US)

(73) Assignee: EMRGE, LLC, Atlanta, GA (US)

( * ) Notice: Subject to any disclaimer, the term of this patent is extended or adjusted under 35 U.S.C. 154(b) by 525 days.

(21) Appl. No.: 16/406,058

(22) Filed: May 8, 2019

(65) Prior Publication Data
US 2019/0261989 A1 Aug. 29, 2019

Related U.S. Application Data

(63) Continuation of application No. 15/659,012, filed on Jul. 25, 2017, now Pat. No. 10,327,774, which is a
(Continued)

(51) Int. Cl.
*A61B 17/08* (2006.01)
*A61B 17/00* (2006.01)
(Continued)

(52) U.S. Cl.
CPC ...... *A61B 17/085* (2013.01); *A61B 17/00491* (2013.01); *A61B 17/064* (2013.01);
(Continued)

(58) Field of Classification Search
CPC ............... A61B 17/085; A61B 17/10; A61B 2017/00862; A61B 2017/00951;
(Continued)

(56) References Cited

U.S. PATENT DOCUMENTS 765,793 A 7/1904 Ruckel
815,264 A 3/1906 Chambers
(Continued)

FOREIGN PATENT DOCUMENTS

AU 2012236205 B2 8/2016
AU 2016262734 12/2016
(Continued)

OTHER PUBLICATIONS

First Chinese Office Action in related CN Application No. 201611102500.1, dated Aug. 20, 2018, 21 pages (including English Translation).
(Continued)

*Primary Examiner* — George J Ulsh
(74) *Attorney, Agent, or Firm* — Additon, Pendleton & Witherspoon, P.A.

(57) ABSTRACT

Medical devices disclosed herein include pre-defined structures for dispensing forces onto a tissue plane in a living organism and are utilized to adjust spatial relationships, orientations, and mechanical forces in a patient treatment area. The treatment area may be a wound, an incision, or a surgically accessed area within a patient that includes oppositely disposed sections that heal more efficiently and with less scarring when force vectors of a particular magnitude and direction are applied to the treatment area. The medical device provides a structure that may be pre-stressed through planned deformation that develops desirable spatial and mechanical relationships along the tissue plane for alignment, compression, advancement, eversion, inversion, distraction, rotation, angulation, and the control or modulation of tension across the treatment area.

15 Claims, 19 Drawing Sheets

Related U.S. Application Data continuation of application No. 14/038,975, filed on Sep. 27, 2013, now abandoned, which is a continuation of application No. PCT/US2012/031638, filed on Mar. 30, 2012.

(60) Provisional application No. 61/470,158, filed on Mar. 31, 2011, provisional application No. 61/469,966, filed on Mar. 31, 2011.

(51) Int. Cl.
*A61B 17/064* (2006.01)
*A61B 17/10* (2006.01)

(52) U.S. Cl.
CPC ..... *A61B 17/10* (2013.01); *A61B 2017/00862* (2013.01); *A61B 2017/00951* (2013.01)

(58) Field of Classification Search
CPC .............. A61B 2017/086; A61B 17/08; A61B 17/00491; A61B 17/064; A61F 13/00; A61F 13/02
USPC ........................................................ 606/216
See application file for complete search history.

(56) References Cited

U.S. PATENT DOCUMENTS

| | | | |
|---|---|---|---|
| 1,248,450 A | 3/1917 | Burke |
| 1,908,229 A | 5/1933 | Dyer |
| 2,254,620 A | 9/1941 | Miller |
| 2,341,121 A | 9/1942 | Schaaff |
| D134,810 S | 1/1943 | Tawdish |
| 2,371,978 A | 3/1945 | Perham |
| 2,421,193 A | 5/1947 | Gardner |
| 2,979,671 A | 6/1954 | Garber, Jr. |
| 2,912,735 A | 2/1957 | Johnson et al. |
| 3,068,870 A | 3/1960 | Levin |
| 3,014,483 A | 12/1961 | McCarthy |
| 3,082,773 A | 3/1963 | Renstrom et al. |
| 3,120,687 A | 2/1964 | Greening et al. |
| 3,487,836 A | 1/1970 | Niebel et al. |
| 3,625,220 A | 12/1971 | Engelsher |
| 3,695,271 A | 10/1972 | Chodorow |
| 3,831,608 A | 8/1974 | Kletschka et al. |
| 3,861,008 A | 1/1975 | Wannag |
| 4,011,639 A | 3/1977 | Koleske |
| 4,275,736 A | 6/1981 | Chodorow |
| D260,681 S | 9/1981 | Chodorow et al. |
| 4,506,669 A | 3/1985 | Blake, III |
| 4,539,990 A | 9/1985 | Stivala |
| 4,646,731 A | 3/1987 | Brower |
| 4,702,251 A | 10/1987 | Sheehan |
| D293,717 S | 1/1988 | Proulx et al. |
| 4,734,320 A | 3/1988 | Ohira et al. |
| 4,742,826 A | 5/1988 | McLorg |
| 4,815,468 A | 3/1989 | Annand |
| 4,825,866 A | 5/1989 | Pierce |
| 5,047,047 A | 9/1991 | Yoon |
| 5,127,412 A | 7/1992 | Cosmetto et al. |
| 5,176,703 A | 1/1993 | Peterson |
| 5,230,701 A | 7/1993 | Meyer et al. |
| 5,236,440 A | 8/1993 | Hlavacek |
| 5,366,480 A | 11/1994 | Corriveau et al. |
| D354,134 S | 1/1995 | Tanaka |
| D359,144 S | 6/1995 | Healzer et al. |
| 5,489,083 A | 2/1996 | Rollor |
| 5,549,713 A | 8/1996 | Kim |
| 5,562,705 A | 10/1996 | Whiteford |
| 5,630,430 A | 5/1997 | Shultz et al. |
| 5,775,345 A | 7/1998 | Chou |
| D407,489 S | 3/1999 | Kalat |
| 5,947,917 A | 9/1999 | Carte et al. |
| 5,947,998 A | 9/1999 | Cartmell et al. |
| 6,176,868 B1 | 1/2001 | Detour |
| 6,196,228 B1 | 3/2001 | Kreitzer et al. |
| 6,559,350 B1 | 5/2003 | Tetreault et al. |
| 6,894,204 B2 | 5/2005 | Dunshee |
| D530,420 S | 10/2006 | Chesnin |
| 7,332,641 B2 | 2/2008 | Lebner et al. |
| 7,683,234 B2 | 3/2010 | Gurtner et al. |
| 8,157,839 B2 | 4/2012 | Riskin et al. |
| 8,183,428 B2 | 5/2012 | Gurtner et al. |
| 8,246,590 B2 | 8/2012 | Hu et al. |
| D667,167 S | 9/2012 | Stewart |
| D671,265 S | 11/2012 | Stewart |
| 8,323,313 B1 | 12/2012 | Belson et al. |
| D674,544 S | 1/2013 | Stewart |
| 8,395,011 B2 | 3/2013 | Zepeda et al. |
| 8,435,221 B2 | 5/2013 | Hu et al. |
| D683,860 S | 6/2013 | Quimby |
| D690,020 S | 9/2013 | Quimby |
| 8,562,576 B2 | 10/2013 | Hu et al. |
| 8,592,640 B2 | 11/2013 | Zepeda et al. |
| 8,674,164 B2 | 3/2014 | Zepeda et al. |
| 8,834,434 B2 | 9/2014 | Hu et al. |
| 8,915,942 B2 | 12/2014 | Zhang |
| 9,028,529 B2 | 5/2015 | Riskin et al. |
| 9,050,086 B2 | 6/2015 | Belson et al. |
| 9,089,328 B2 | 7/2015 | Belson et al. |
| 9,119,620 B2 | 9/2015 | Peterson et al. |
| D754,862 S | 4/2016 | Huff |
| 9,301,760 B2 | 4/2016 | Fox |
| 9,421,133 B2 | 8/2016 | Hu et al. |
| 9,492,171 B2 | 11/2016 | Petenaude |
| 9,517,163 B2 | 12/2016 | Goldman et al. |
| D780,317 S | 2/2017 | Vandervoort |
| 9,603,596 B2 | 3/2017 | Riskin et al. |
| 9,649,226 B2 | 5/2017 | Zepeda et al. |
| D790,072 S | 6/2017 | Hiebert |
| D811,609 S | 2/2018 | Huff |
| D815,747 S | 4/2018 | Kellock et al. |
| 9,974,532 B2 | 5/2018 | Baas et al. |
| 10,064,616 B2 | 9/2018 | Lear et al. |
| D831,220 S | 10/2018 | Chase et al. |
| 10,213,350 B2 | 2/2019 | Jackson et al. |
| 10,327,774 B2 | 6/2019 | Eaves |
| 10,426,479 B2 | 10/2019 | Vold et al. |
| 10,517,768 B2 | 12/2019 | Zepeda et al. |
| D876,641 S | 2/2020 | Eaves, III et al. |
| D876,653 S | 2/2020 | Heller |
| D918,400 S | 5/2021 | Ma |
| 2002/0111641 A1 | 8/2002 | Peterson et al. |
| 2003/0221700 A1 | 12/2003 | La Fauci |
| 2005/0080453 A1 | 4/2005 | Lebner |
| 2005/0193527 A1 | 9/2005 | Gould |
| 2006/0200198 A1 | 9/2006 | Riskin et al. |
| 2009/0125052 A1 | 5/2009 | Pinna et al. |
| 2009/0151128 A1 | 6/2009 | Gould |
| 2009/0240186 A1 | 9/2009 | Frang |
| 2009/0259203 A1 | 10/2009 | Hu et al. |
| 2010/0051046 A1 | 3/2010 | Stevenson et al. |
| 2010/0081983 A1 | 4/2010 | Zocher |
| 2010/0228287 A1 | 9/2010 | Jeekel |
| 2010/0236566 A1 | 9/2010 | Stachowski |
| 2010/0262126 A1 | 10/2010 | Hu et al. |
| 2011/0004173 A1 | 1/2011 | Hu et al. |
| 2011/0023906 A1 | 2/2011 | Tu |
| 2011/0040325 A1 | 2/2011 | Moehrle |
| 2011/0054547 A1 | 3/2011 | Anderson |
| 2011/0105963 A1 | 5/2011 | Hu et al. |
| 2011/0152738 A1 | 6/2011 | Zepeda et al. |
| 2012/0172779 A1 | 7/2012 | Spinelli et al. |
| 2012/0221044 A1 | 8/2012 | Archibald et al. |
| 2013/0150899 A1 | 6/2013 | Sixto, Jr. et al. |
| 2013/0178897 A1 | 7/2013 | Wu et al. |
| 2013/0282049 A1 | 10/2013 | Peterson et al. |
| 2014/0066943 A1 | 3/2014 | Sixto, Jr. et al. |
| 2014/0107597 A1 | 4/2014 | Hu et al. |
| 2014/0128819 A1 | 5/2014 | Eaves |
| 2014/0227483 A1 | 8/2014 | Eaves |
| 2014/0243901 A1 | 8/2014 | Mebarak et al. |
| 2014/0336701 A1 | 11/2014 | McLorg |
| 2015/0005722 A1 | 1/2015 | Hu et al. |

(56) References Cited

U.S. PATENT DOCUMENTS

| | | |
|---|---|---|
| 2015/0112311 A1 | 4/2015 | Hammond et al. |
| 2015/0305739 A1 | 10/2015 | Rolandi et al. |
| 2016/0324693 A1 | 11/2016 | Hu et al. |
| 2017/0071596 A1 | 3/2017 | Lear et al. |
| 2018/0125492 A1 | 5/2018 | Eaves |
| 2018/0303483 A1 | 10/2018 | Zhang |
| 2018/0338757 A1 | 11/2018 | Lear et al. |
| 2018/0353335 A1 | 12/2018 | Walker |
| 2019/0133582 A1 | 5/2019 | Eaves et al. |
| 2019/0261989 A1 | 8/2019 | Eaves |

FOREIGN PATENT DOCUMENTS

| | | |
|---|---|---|
| CA | 2830918 A1 | 10/2012 |
| CN | 1889903 A | 1/2007 |
| CN | 101606856 | 12/2009 |
| CN | 101606856 A | 12/2009 |
| CN | 101828939 B | 9/2010 |
| CN | 201683935 U | 12/2010 |
| CN | 103892877 A | 7/2014 |
| CN | 104755033 A | 7/2015 |
| CN | 105147344 A | 12/2015 |
| CN | 205144638 U | 4/2016 |
| CN | 103533900 A | 12/2016 |
| EP | 2691029 A2 | 2/2014 |
| FR | 419096 | 10/1910 |
| FR | 794710 | 2/1936 |
| FR | 794710 A | 2/1936 |
| JP | 2011-500170 A | 1/2011 |
| JP | 2014-516288 | 7/2014 |
| KR | 10-2009-0066415 A | 6/2009 |
| KR | 10-2014-0020993 | 2/2014 |
| TW | M340039 U | 9/2008 |
| WO | 02/26181 A1 | 4/2002 |
| WO | 2006/124671 A2 | 11/2006 |
| WO | 2009049232 A1 | 4/2009 |
| WO | 2011019859 A2 | 2/2011 |
| WO | 2011019859 A2 | 2/2011 |
| WO | 2013188884 A1 | 6/2012 |
| WO | 2012/135735 | 10/2012 |
| WO | 2013/059600 | 4/2013 |
| WO | 2013/059600 A1 | 4/2013 |
| WO | 2018/075879 A1 | 4/2014 |
| WO | 2014/070922 A1 | 5/2014 |
| WO | 2017/079782 A1 | 5/2017 |
| WO | 2018/075879 | 4/2018 |
| WO | 2021/072021 A1 | 4/2021 |

OTHER PUBLICATIONS

Kyle Design, Hair Barrettes Made in France—Extra Large 4" Blank Metal, No date specified, https://www.kyledesigns.com/hair-barrettes-made-in-france-extra-large-4-blank-metal/ (Year: 0) 4 pages.
International Preliminary Report on Patentability in commonly owned International Application No. PCT/US2017/057569, dated May 2, 2019, pp. 1-6 [All references previously cited.].
Amazon, "Elastic Bandage Wrap Compression Tape", Review by Maria A. Dec. 18, 2017, <URL:https://www.amazon.com/Elastic-Bandage-Wrap-Compression-Tape/dp/B06XQ8BY8?th=1> (Year: 2017) 12 pages.
Examination Report No. 1 in related Australian Application No. 2016262734, dated Jan. 14, 2019, 3 pages.
Extended Search Report in related EP Application 12762897.2, dated May 27, 2015, 11 pages.
Japanese Office Action in related JP Application No. 2014-502866, dated Dec. 10, 2015, Translation provided, 11 pages.
Chinese First Office Action in related CN Application No. 201280017051.4, dated Jun. 1, 2015, Translation provided, 13 pages.
Chinese Second Office Action in related CN Application No. 201280017051.4, dated Dec. 31, 2015, Translation provided, 8 pages.

Australian Patent Examination Report No. 1 in related Australian Patent Application No. 201226205, dated Aug. 28, 2015, 5 pages.
International Search Report and Written Opinion issued in commonly owned PCT/US2012/031638 dated Nov. 29, 2012; 10 pages.
Supplementary Partial European Search Report in commonly owned EP Application No. 12762897, dated Dec. 23, 2014, 7 pages.
Japanese Notice of Reasons for Rejection in related JP Application No. 2014-502866, dated Oct. 3, 2016; 9 pages.
Southmedic Inc., SutureSafe Instructions for Use, 2 pages [Downloaded Jul. 25, 2017 from http://dynamictissuesystems.com/wp-content/uploads/2015/09/IFU0251_E.pdf].
SutureSafe Inc., Product Brochure SutureSafe Support closed wounds and provide stability; 2 pages [Downloaded Jul. 25, 2017 from http://dynamictissuesystems.com/wp-content/uploads/2015/09/SutureSafe-SS-lr2.pdf].
Search Report in counterpart PCT Application No. PCT/2018/057569, dated Feb. 2, 2018, pp. 1-6.
Written Opinion in counterpart PCT Application No. PCT/2018/057569, dated Apr. 26, 2018, pp. 1-5.
Commonly owned Design U.S. Appl. No. 29/622,936, filed Oct. 20, 2017, pp. 1-56.
Commonly owned Design U.S. Appl. No. 29/622,941, filed Oct. 20, 2017, pp. 1-57.
Supplementary Partial European Search Report in related EP Application No. 12762897, dated Dec. 23, 2014, 7 pages.
Commonly owned U.S. Appl. No. 16/153,340, filed Oct. 5, 2018, pp. 1-111.
Summons to attend oral proceedings in counterpart European Application No. 12762897.2 dated Mar. 22, 2021, pp. 1-11 [All references previously cited ].
Partial Supplementary European Search Report in related European Application No. 17861546.4 dated Apr. 22, 2020, pp. 1-12 [US Publication No. 2014/0128819 previously cited.].
International Search Report and Written Opinion in commonly owned International Application No. PCT/US20/54702 dated Mar. 11, 2021, pp. 1-28.
Knott et al., "Curved bistable composite slit tubes with positive Gaussian curvature", University of Surrey, Guilford, United Kingdom, pp. 1-22.
Jiang et al., "Snapping of bistable, prestressed cylindrical shells", A Letters Journal Exploring, www.epljournal.org, Jun. 2018, EPL, 122 (2018) 64003, pp. 1-8.
Kebadze, et al., "Bistable prestressed shell structures", International Journal of Solids and Structures, www.elsevier.com/locate/ijsolstr, 41 (2004) pp. 2801-2820.
Kim et al., "Flytrap-inspired robot using structurally integrated actuation based on bistability and developable surface", Bioinspiration & Miomimetics, 9 (2014) 036004, pp. 1-15.
Seffen, "Morphing bistable orthotropic elliptical shallow shells", Proceedings of the Roayl Society, (2007) 463, 67-83, pp. 1-17.
International Preliminary Report on Patentability in commonly owned International Application No. PCT/US2017/057569, dated May 2, 2019, pp. 1-6.
Search Report in related European Application No. 17861546.4 dated Jul. 31, 2020, pp. 1-10 [All references previously cited.].
Extended Search Report for related EP Application 12762897.2, dated May 27, 2015, 11 pages [previously submitted in parent].
Japanese Office Action for related JP Application No. 2014-502866, dated Dec. 10, 2015, Translation provided, 11 pages [previously submitted in parent].
Chinese First Office Action for related CN Application No. 201280017051.4, dated Jun. 1, 2015, Translation provided, 13 pages [previously submitted in parent].
Chinese Second Office Action for related CN Application No. 201280017051.4, dated Dec. 31, 2015, Translation provided, 8 pages [previously submitted in parent].
Australian Patent Examination Report No. 1 in related Australian Patent Application No. 201226205, dated Aug. 28, 2015, 5 pages, [previously submitted in parent].
International Search Report and Written Opinion issued in PCT/US2012/031638 dated Nov. 29, 2012; 10 pages [previously submitted in parent].

(56) References Cited

OTHER PUBLICATIONS

Supplementary Partial European Search Report for EP Application No. 12762897, dated Dec. 23, 2014, 7 pages. [previously submitted in parent].
Japanese Notice of Reasons for Rejection in related JP Application No. 2014-502866, dated Oct. 3, 2016; 9 pages. [previously submitted in parent].
Southmedic Inc., SutureSafe Instructions for Use, 2 pages [Downloaded Jul. 25, 2017 from http://dynamictissuesystems.com/wp-content/uploads/2015/09/IFU0251_E.pdf] [previously submitted in parent].
SutureSafe Inc., Product Brochure SutureSafe Support closed wounds and provide stability; 2 pages [Downloaded Jul. 25, 2017 from http://dynamictissuesystems.com/wp-content/uploads/2015/09/SutureSafe-SS-lr2.pd] [previously submitted in parent].
Examination Report No. 1 in related Australian Application No. 2016262734, dated Jan. 14, 2019, 3 pages [previously submitted in parent].
First Chinese Office Action in related CN Application No. 201611102500.1, dated Aug. 20, 2018, 21 pages (including English Translation) [previously submitted in parent].

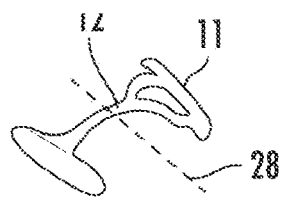
FIG. 19P
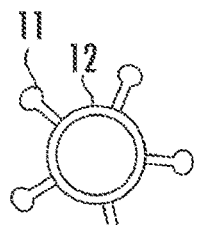
FIG. 19Q
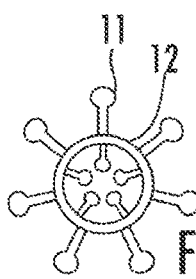
FIG. 19R
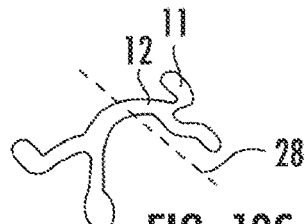
FIG. 19S
FIG. 19T
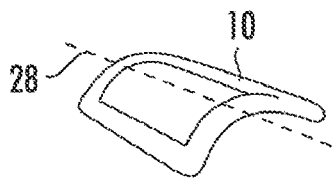
FIG. 19U
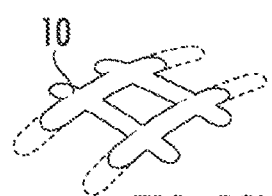
FIG. 19V
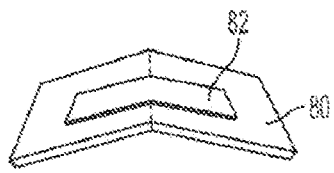
FG. 20A
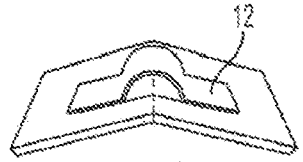
FG. 20B
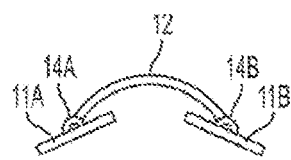
FIG. 21A
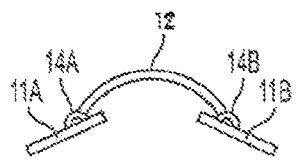
FIG. 21B
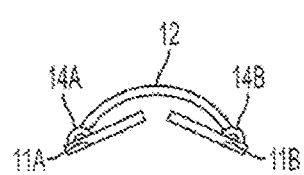
FIG. 21C
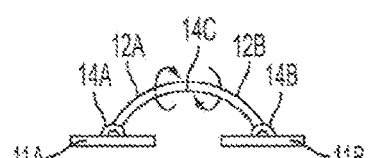
FIG. 21D

FORCE MODULATING TISSUE BRIDGE

CROSS REFERENCE TO PRIORITY APPLICATIONS

This application is a continuation of U.S. patent application Ser. No. 15/659,012 for a Force Modulating Tissue Bridge, filed Jul. 25, 2017, (and published May 10, 2018, as U.S. Patent Application Publication No. 2018/0125492), which is itself a continuation of U.S. patent application Ser. No. 14/038,975 for a Force Modulating Tissue Bridge, filed Sep. 27, 2013, (and published May 8, 2014, as U.S. Patent Application Publication No. 2014/0128819), which is a continuation of International Patent Application No. PCT/US12/31638 for a Force Modulating Tissue Bridge, filed Mar. 30, 2012, (and published Oct. 4, 2012, as International Publication No. WO 2012/135735), which itself claims the benefit of U.S. Patent Application No. 61/469,966 (filed Mar. 31, 2011) for a Pre-Tensioned/Pre-Stressed Device and U.S. Patent Application No. 61/470,158 (filed Mar. 31, 2011) for a Device and Method for Applying a Pre-Tensioned Element to Opposing Surfaces. Each of the foregoing patent applications and patent application publications is hereby incorporated by reference in its entirety.

FIELD OF INVENTION

The present invention relates to a medical device for approximation, alignment, distraction, fixation, or compression of opposing regions along a tissue plane. In particular, the device relates to a medical device that is manufactured in a first at-rest shape and state, that is deformed prior to placement on a tissue plane in a patient, and that reverts back toward the at rest shape upon placement, thereby providing tissue-shaping forces across a treatment area.

BACKGROUND

Many kinds of medical treatments incorporate devices that hold parts of the body in a particular configuration for healing. For example, cuts, wounds, and surgical incisions benefit from being held together in a fixed arrangement to promote efficient healing and to minimize scarring. Throughout the centuries many mechanisms have been created to align opposing tissue planes. Other devices include adhesives, clamps, screws, rods, staples, tapes, cord-like elements (sutures, ligature), or other mechanisms. Each of these approaches has a range of different qualities that may include flexibility versus rigidity, loose alignment versus compression, inversion versus eversion of a plane, external versus internal application, and permanent versus temporary application of devices. Many of these approaches require that the opposing elements be aligned prior to fixation (e.g. tapes, adhesives) while in other instances the elements are aligned as the fixation is applied (e.g. sutures, staples).

A wide variety of strategies and mechanisms have been employed to affect and control relationships between tissue planes and thus promote desired therapeutic effects. For example, U.S. Pat. No. 4,702,251 (Sheehan 1987) illustrates the use of a bandage that adheres to a patient's skin and forms a bridge over a tissue plane to align and evert the skin. United States Patent Publication No. 20090240186 (Fang) discloses a bandaging device that includes sections attached to either side of a wound and a lifting portion that is grasped to pull the wound sections together. See also, U.S. Pat. No. 815,264 (Chambers 1906) (disclosing a suture bridge); U.S. Pat. No. 2,371,978 (Perham 1941) (disclosing a clamp for retaining the edges of a wound); and U.S. Pat. No. 3,487,836 (Niebel 1968) (disclosing a surgical strip stitch). The lifting portion includes sections of the bandage that adhere to one another to apply approximating forces onto opposite sections of a wound.

The repair of a surgical or traumatic wound by the approximation of the wound margins is a prototypical example, and in this action the tissue planes need to be brought into alignment with the appropriate degree of tension to promote wound healing without adversely affecting tissue perfusion. Eversion of the wound margins, such as in closure of skin wounds, supports wound healing, the approximation of the deeper subcutaneous tissue margins, and an optimal scar appearance. Advancement of tissues to close tissue defects, compression of tissues to promote healing (e.g. treatment of fractures or reduction in hypertrophic scars and keloid scars), and distraction or expansion of tissues to alter tissue dimensions are all additional examples of actions where the relationships between tissue planes and the forces acting upon them need to be controlled.

Heretofore many devices and mechanisms have been utilized toward these goals, and the device or mechanism selected can differ significantly in order to address the specific clinical situation, the characteristics of the tissues being treated, and other factors. Surgical needles and sutures, surgical staples, adhesives, tapes, rigid plates and screws, rods, clips, tissues expanders, and distracters are all examples of the variety of devices and mechanisms that can be employed to position and control tissues for therapeutic purposes. With any given tissue type and clinical situation more than one of these options may be considered, each having advantages and disadvantages. In a given situation factors that may represent advantages are ease of application, stability or security of approximation, adjustability, point-to-point approximation, and an a-traumatic device-tissue interface. Similarly, factors that may represent disadvantages are increased cost and complexity, the persistence of device elements (foreign body) within the wound bed that could adversely affect healing or the risk of infection, the necessity of device removal, and pain upon application or removal with a subsequent requirement for anesthesia. Other characteristics of the wound treatment or closure mechanisms can affect the healing of the wound or the appearance of the scar, such as the relative elasticity of the closure to allow responses to mechanical forces, the inflammatory reaction that may be generated by hydrolysis of absorbable closure materials, and the pressure points or tissue perforation points that create new points of scaring outside of the immediate tissue healing zone.

In addition to the need to control the orientation and alignment of tissues, the mechanical environment of the tissues significantly affects healing. Increased tension across a healing wound not only leads to an increase in the risk of wound dehiscense in the acute treatment period, but also significantly affects the wound healing process chronically, leading to increased scaring and an increased risk of hypertrophic scars and keloids. Factors which increase wound tension tend to have poorer scaring characteristics, examples of which include the presence of chronic swelling, gravitational forces (e.g. a sternal wound location which is impacted by the weight of the breasts) or mechanical forces (e.g. over the extensor surface of a joint where normal joint motion may increase the tension on the skin). Incisional closures, where no tissue is removed and subsequently tension is less, tend to have better scaring characteristics than excisional procedures, wherein removal of tissues increased the subsequent wound closure tension. Increased wound tension has been demonstrated to lead to an increased number of fibroblasts, increased collagen deposition, alterations in the orientation of fibroblasts, and changes in the level of certain bio-chemicals, among other effects. Reducing the tension on healing wounds by mechanical means is an accepted strategy to assist healing and scar appearance. In addition to the reduction of tension, in some circumstances a compressive mechanical environment is utilized in treatment, such as in the treatment of established hypertrophic scars and keloids or in the treatment of osseous wounds (bone fractures or osteotomies).

Along these lines, one example of a device that is used to direct planned forces onto a tissue plane is set forth in published United States Patent Publication No. 20120035521 (Zepeda 2012). The Zepeda application discloses a kit that includes a bandage applicator that applies a predetermined strain across a bandage placed onto a patient's injured skin. The engineered strain in the bandage is applied to the skin after attaching the bandage to the skin and removing the bandage applicator. The bandage applicator has numerous parts and connectors that must be configured prior to use and increase the complexity of the device.

In the art of medical devices used for tissue treatment, there continues to exist a need for a medical device that is capable of applying a particularly directed force vector across a tissue plane without the need for cumbersome and costly connected pieces and parts within the device.

SUMMARY

Accordingly, there is provided a medical device for approximation, alignment distraction, fixation, stabilization, or compression of opposing members comprising: a central section capable of compression and decompression; lateral sections on each side of the central section; and areas on the device for attaching the device directly to a patient's tissue. The device has a pre-defined shape and state when at rest and is capable of distortion or deformation to load particularly engineered potential force into the device for application to a tissue plane. In one embodiment, the deformation is accomplished by distorting the shape of the device and adjusting the distance between opposite sides of the central section or the distance between the lateral sections that attach to a patient. Upon application to the patient, the potential forces in the device are released as the device reverts back toward its original at-rest state. The connection between the device and the tissue plane resists the device's natural tendency to revert to an at-rest position and yields a desired resultant force along the tissue plane. Depending upon the direction and magnitude of the potential forces loaded into the device by deformation, the resultant forces on the tissue plane move sections of the tissue plane to desired positions for more efficient healing and/or less scarring.

Loading potential forces into the device may be accomplished by squeezing or compressing sides of the device together before applying the device to a tissue plane. As the device tends to open back up to return to an at-rest state, the device provides a distracting or opening force across a treatment area. Alternatively, the device may be stretched or opened from side to side so that, upon application to a tissue plane, the device provides a closing or approximating force across a treatment area. The size and magnitude of the resultant forces on a tissue plane are pre-planned by applying appropriate deformation forces to the medical device prior to attaching the device over a treatment area.

In one embodiment, the medical device is a tissue bridge that connects to a tissue plane along attachment zones on an underside of the device. The device includes a central section that connects to opposite lateral sections, and the underside of each lateral section includes a respective attachment zone for direct placement on a tissue plane such as a patient's skin or other anatomic structure. The central section is designed to extend over a treatment area. Transitional sections, or shoulders, extend from the central section to the lateral sections to provide a continuous structure that may be formed in a single piece construction. The shape of the central, transitional, and lateral sections may be customized to provide a desired resultant force across a treatment area.

The tissue bridge may be deformed to load potential forces into the structure prior to placing the tissue bridge onto a tissue plane. The deformation may be accomplished manually, mechanically, or with the assistance of a tissue bridge applicator. The applicator provides a convenient tool for engaging the tissue bridge, providing a deformational force to load the tissue bridge with potential energy, applying the tissue bridge to a tissue plane, and then separating from the tissue bridge as necessary or desired.

In yet another embodiment of the invention, the tissue bridge may incorporate a two-piece construction in which a tissue bridge connects to an elastomeric strip that adheres to a patient (e.g., a bandage). By deforming the tissue bridge and loading potential force therein, the two piece construction also stretches or deforms the elastomeric strip for placing on a tissue plane across a treatment area. In this way, the elastomeric strip and the tissue bridge provide medical intervention across the tissue plane. In this embodiment, the tissue bridge may be held in place with the elastomeric strip or removed to reduce resultant force across the tissue plane.

The two piece embodiment may be configured as a combination of a tissue bridge and a bandage. The tissue bridge may have an arcuate shape or may be a flat body adhering to the bandage. In one configuration, the tissue bridge and the elastomeric bandage are both flat so that neither the bridge nor the bandage are under any tension in an at-rest state and are conducive to folding without deforming either component. Generally known adhesives of varying strength may be used to attach the bandage to the tissue plane and to attach the tissue bridge to the bandage. The connection between the tissue bridge and the bandage may allow for the tissue bridge to be peeled off the bandage after the bandage is applied to a treatment area.

The tissue bridges disclosed herein are useful as stand-alone devices or used in combination with one another. In another embodiment, a plurality of tissue bridges may be arranged across a tissue plane to provide scaffolding for placing layered materials (e.g., bandages, adhesive sheets, medicinal sheets) over the series of tissue bridges. For embodiments in which the tissue bridges include raised portions over a treatment area, the series of tissue bridges may support an adhesive sheet so that the tissue bridges and the overriding sheet form a conduit with a space defined between the treatment area and the sheet. This space may be used for additional medical intervention as described below (i.e. drainage, irrigation, inspection, application of medicines and anesthesia).

Overall, the devices disclosed herein function for force transmission and modulation across a bridge or conduit between tissue planes acting through zones of attachment. The tissue bridge can assume a wide variety of designs dependent upon the characteristics of the tissues being treated, the method of attachment to the tissue planes, the geometric configuration of the device, the direction and magnitude of the forces required, the component material(s) or tissue(s) properties, aesthetics, secondary attachment requirements or other factors. In order to generate different summary force vectors, effective attachments and geometric configurations required for different clinical situations, each these characteristics can be modified independently or in any combination thus producing a spectrum of configurations, embodiments, and effects, and the vast array of such variations are obvious to ones skilled in the art.

The tissue bridge disclosed and claimed herein exerts its effect through a "pre-loading" or "pre-tensioning" process whereby the bridge and/or the tissue planes being addressed are subjected to a deformational force that is applied prior to the time of device fixation and that is released after partial or total fixation of the device to the tissue planes. Upon release of this deformational force the potential forces thus generated within the device and/or tissues are released to act upon the tissue planes until such time that the device is removed, absorbed, released, detached, or tissue characteristics change such that the device is brought into a non-tensioned configuration.

The resultant vectors applied to the tissue planes are a function of the rotational stiffness of the device (k=M/Ø) as a function of the device dimensions, geometry, and the elastic modulus of the construction materials; the method, amplitude, direction and positioning of the pre-leading force applied prior to application; the points and method of fixation to the tissue planes; and mechanical tissue characteristics. The deformational force can be applied to the bridge or to the tissues, or can be applied to both the bridge and the tissues. When the deformational "pre-loading" or "pre-tensioning" force is applied to a tissue bridge, it is applied in a manner such that the force does not exceed the yield point of the device, and upon tissue plane attachment and release of the deformational force the potential energy thus transferred to the bridge can exert its effect on the tissues. When a force is applied directly to the tissues, external mechanical forces are applied to the tissues to control their position and force environment in relationship to the bridge prior to the time of attachment. When the force is applied only to the tissues, the bridge may be either of a non-elastic or elastic construction.

In addition to controlling the forces and spatial relationships between the tissues upon release (static control or static shielding), the bridge also functions to control the mechanical forces to which the tissues may be subjected after application (dynamic control or dynamic shielding). For instance, if there is tissue swelling centrally near the junction where the planes are brought into proximity by the bridge, the elastic nature of the bridge allows this increased pressure to be relieved by undergoing a compensatory distortion in proportion to the force generated within the tissues, thus relieving the tissue tension. If the tissues are subjected to a laterally directed force vector, i.e. when there is a distracting force such as with lateral tissue swelling or resulting from movement in the tissue planes, the bridge can also distort in relation to the applied force vectors, thus absorbing the force and shielding the junction area from said forces. If a centrally directed force vector, i.e. a compressing force, is applied from either one or both sides of the tissue plane junction, the bridge can undergo a centrally directed distortion, with the absorption of the external compression proportional to the distortional force applied. In this way the bridge provides both dynamic response to changes in tissue forces and a dynamic shielding of the zone near the intersection between the tissue planes as well as static tension control and shielding when the mechanical environment is not in flux.

If the bridge is of a rigid design, any asymmetric forces lateral to the bridge can be transmitted to the opposite side, and likewise the zone near the intersection between the tissue planes is shielded. When the bridge has some degree of elasticity and a lateral tissue force vector is applied in an asymmetric manner, the dispersion of forces will be a combination of deformation force absorption within the bridge as well as transmission of the forces through the structure of the bridge to the tissue(s) on the opposite side. In these manners the device functions as a force conduit.

The bridge has a central section or sections, or body(ies), and lateral sections, or limbs which are connected at a transition zone. Each of these sections can be of different dimensions, appearances, curves, angles, or appearance as dictated by specific clinical needs and tissue characteristics. The device is non-linear such that the central section is not in the same plane as the lateral sections, and may rest above a line drawn between the lateral segments, to the side of a line drawn between the lateral segments, or at other angles in relationship to the surface of the affixed tissue planes. The device may or may not demonstrate bilateral symmetry. Within a given device the lateral segments may be identical design or variable design, and the lateral sections can vary in number, orientation, dimension, materials, construction, or method of fixation.

In one embodiment, the central section demonstrates an outward curve, and the transition zone demonstrates an opposite, inward curve. By making the height of the apex of the central section above the attachment surfaces greater, the arch of rotation of the device with deformational force is lengthened. By making the central section thicker or wider, or modifying it with ridges or other supplementary supports, the relative rotational stiffness of the central section is increased which will modify the magnitude of the deformational force required to generate the same degree of central section deformation upon preloading. Other points of relative strength and weakness may be so configured as to create areas of deformation and areas that are not subject to deformation. Multiple curves or angles may be incorporated into the central section, and holes, slots, grooves, ridges, depressions, or other features can be used to provide secondary functions, such as suspension of tissues, interaction with an applicator device, or to facilitate supplemental fixation, such as sutures or staples.

Like the central section, the transition zone and lateral sections can be of virtually infinite shape, feature, and surface characteristics, and modifying these features affects the force transmission and functioning of the device. For example, the shoulder can be configured to be straight (i.e. in alignment with the lateral segment) and simultaneously relatively thin and therefore more flexible, it may produce the shape and function of a transition curve between the central and lateral segments. Similarly, the lateral segments can be made thicker close to the transition curve, thus providing effective force transmission, but thinner away from the transition curve, thus facilitating attachment of the device. The lateral section can demonstrate slots, grooves, notches, holes, pins, hooks, or other features that facilitate attachment both to the tissue planes and for secondary functions. The lateral section can also contain extensions, such as attached meshes, tapes, adhesive strips, struts, or other features that can facilitate in attachment or function.

The lateral sections can attach to the central section in a variety of configurations so as to produce the desired shape both in the pre-loading, loaded (distorted), and applied situations. By modifying the location and zone of attachment the application and method of use can be altered in a wide variety of ways. For example, if the zone of attachment is at the midpoint of the length of the lateral section, the distorting force can be so applied that both a flattening of the central section as well as an increased angulation of the transition point between the central segment and the lateral section can be produced. This increases the distance between the medial heads of the lateral segment in the pre-application configuration, so that when the device is applied, the medial heads of the lateral segments contact the tissue planes first, then as the transition angle is resumed upon release of the distortion force, the attached tissues are advanced medially and the remainder of the lateral section can then be attached. This central advancement can either create a desired tension reduction upon the tissues in the centrally located zone, or if a greater advancement is created then an actual compressive force can be applied. In an alternate embodiment, if the transition point between the central and lateral segments is near the lateral terminus of the lateral segment, then this creates a longer arc of rotation. Altering the relative elasticity or rigidity of the transition zone, the angle or curve at which it is attached, the resultant angle between the central segment and the lateral segment, or any combination of these can alter the resulting forces generated upon application and the responses to changes in the mechanical tissue environment. For example, if the zone of transition between the central and lateral segments is made very flexible or articulated, and the lateral section is adhered to the tissue planes, a lateralizing force will not affect the relative eversion or inversion of the lateral limb, as with its attachment being flexible it will simply passively follow the direction changes of the lateral tissue planes. All of the lateralizing tissue tension force will be transmitted to the central segment. Alternatively, if the zone of transition between the central and lateral segments is made relatively rigid, both the central and lateral sections as well as the transition zone will all undergo a deformational force absorption change.

Other configurations or structural features can be similarly conceived so as to change the response of the device to deformational loading, tissue force interactions, and post-application mechanical force changes. These include, but are not limited to, articulations, joints, pivot points, dimension changes, curves, angles, bends, twists, points of relative strength or weakness, structural reinforcements, points of applicator attachment, or other design elements.

BRIEF DESCRIPTION OF THE DRAWINGS

Having described the invention in general terms, reference will now be made to the accompanying drawings, which are not necessarily drawn to scale, and wherein:

FIGS. 20A-20B illustrate a tissue bridge applicator for preloading a tissue bridge with force and applying the tissue bridge to a patient.

FIGS. 21A-21D illustrate embodiments of tissue bridges as disclosed herein with hinged and rotatable joints.

FIGS. 22A-22B illustrate a tissue bridge defining an opening in a central section and accommodating a medical instrument there through.

DETAILED DESCRIPTION

The present invention now will be described more fully hereinafter with reference to the accompanying drawings, in which preferred embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art. Like numbers refer to the elements throughout.

The present invention relates to a device, referred to herein as a tissue bridge (10), for alignment, approximation, fixation and/or compression/distraction of portions of a tissue plane (5). It should be understood that while the tissue bridge (10) may be designed to align and fix numerous and different kinds of elements, for the purpose of explaining the subject invention, its applicability to wound healing will be used.

In a first embodiment illustrated in FIGS. 1-9, the device is a tissue bridge (10) that directs resultant forces onto a tissue plane (5) and particularly across a treatment area (28). For purposes of this disclosure, the term "tissue plane" encompasses all kinds and combinations of tissue in patients. The "tissue plane" is not limited to any one surface or kind of tissue but is intended to generally refer to points in a patient's body on which a tissue bridge may be connected. A tissue plane may include, without limitation, more than one surface in or on a patient's body. In one embodiment, the tissue bridge (10) may be formed in a single piece construction such that the transitions between sections of the device are smooth (i.e., the tissue bridge (10)) may not require separately assembled parts and connectors). Many commonly used techniques are available to produce the tissue bridge (10), including but not limited to injection molding, stamping, precision cutting, or any other process that generates a single piece construction.

The tissue bridge (10) set forth herein is described in regard to its application to a tissue plane (5) and across a treatment area (28). The terms "tissue plane" and "treatment area" are intended to encompass all commonly used meanings of the terms and are not limiting of the invention or the environments in which it is used. For example, a tissue plane (5) encompasses, without limitation, all anatomical features of a human or animal, such as the skin, other organs, or the interfaces within the anatomy (e.g., the interface between bones and muscle). The treatment area (28) extends across generalized regions of the anatomy and includes any portion of a tissue plane affected by application of a tissue bridge (10) onto a patient.

Figure 6:
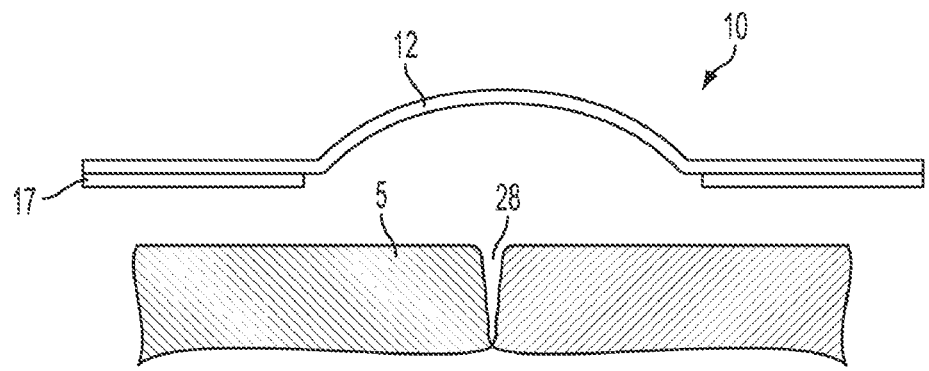
FIG. 6 illustrates a tissue bridge and adhesive combination of FIG. 5 preloaded by deformation for application onto a tissue plane.
Figure 7A:
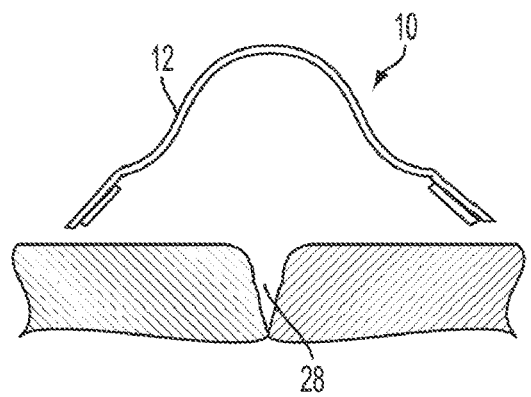
FIGS. 7A-7D illustrates a sequence of deforming a tissue bridge from an at rest state to application on a tissue plane in accordance with the invention herein.
Figure 7B:
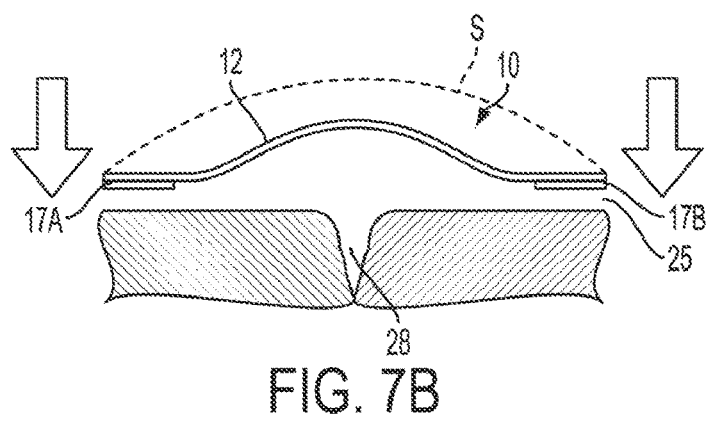
Figure 7C:
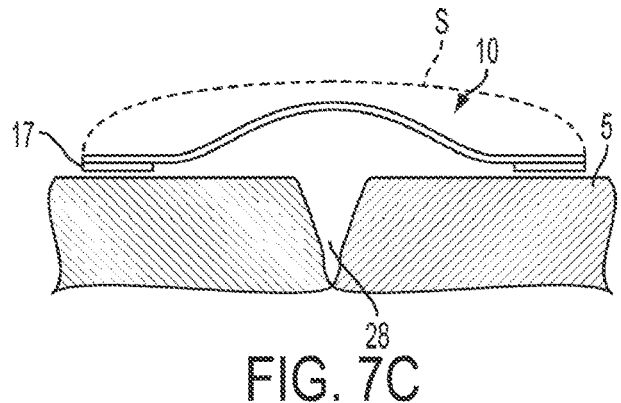
Figure 7D:
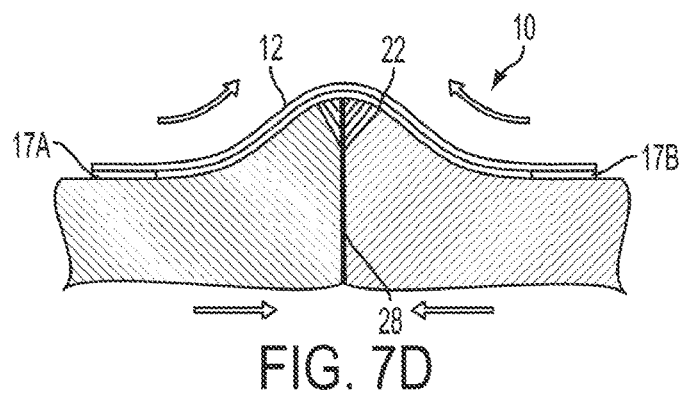
Figure 8:
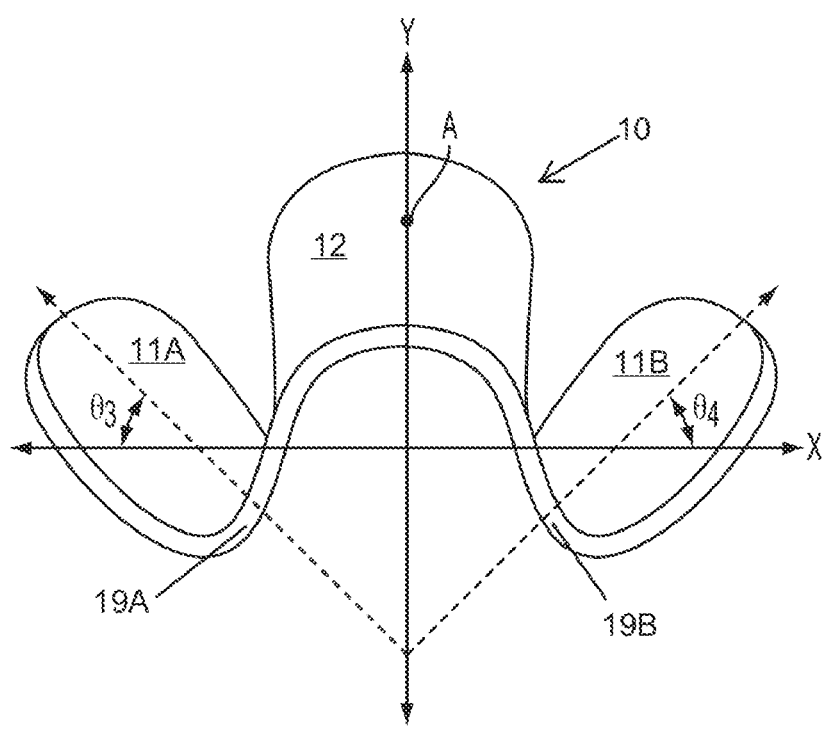
FIG. 8 illustrates a tissue bridge having angled lateral sections in an at rest state according to the disclosure herein.

FIGS. 1-9 show the overall concept of a tissue bridge and one kind of use as a medical device in the context of wound healing. FIGS. 1A and 1B show a first configuration of a tissue bridge (10) in an at-rest state prior to deployment onto a tissue plane. Similarly, FIG. 8 provides more detailed features of another embodiment of a similar device. In all embodiments of the tissue bridge (10), the resultant forces on a tissue plane (5) are pre-engineered within the tissue bridge (10) to produce a desired effect on a tissue plane (5). For example, FIGS. 6, 7, and 9 illustrate the tissue plane (5) as encompassing opposite sides of a wound or incision across which the tissue bridge (10) extends and directs pre-planned forces.

Figure 1A:
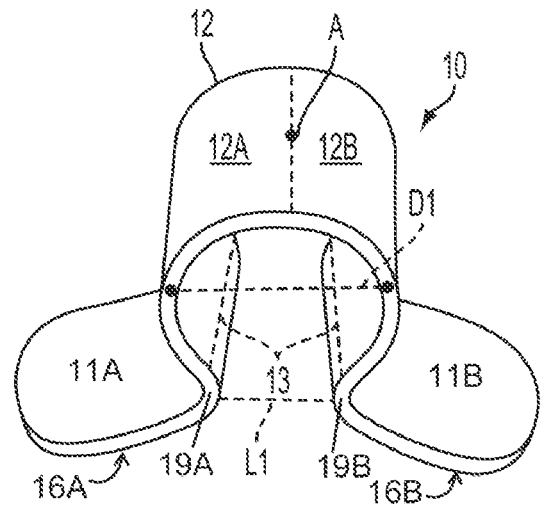
FIGS. 1A-1B show a perspective view of a tissue bridge as disclosed herein.
Figure 1B:
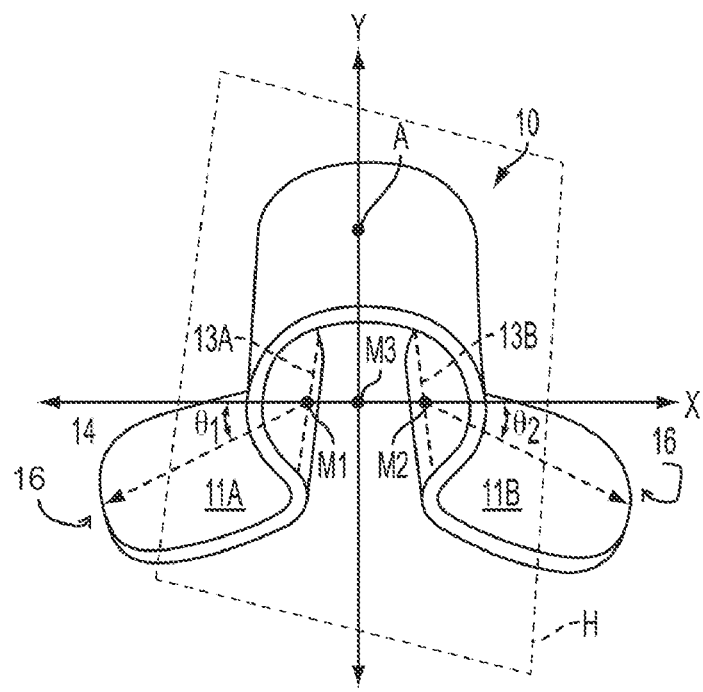
Figure 2:
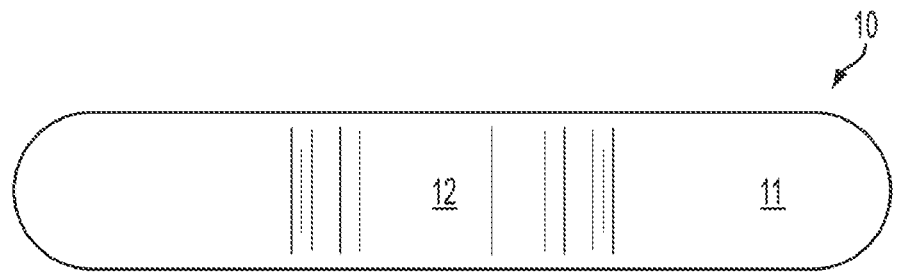
FIG. 2 shows a top plan view of a tissue bridge as disclosed herein.

Starting with FIG. 1A and FIG. 1B, a tissue bridge (10) is capable of directing forces onto a tissue plane (5) to accomplish a desirable healing effect as previously noted. The tissue bridge (10) includes a central section (12) that would extend over a treatment area (28) on a patient. The central section (12) includes an uppermost region, or apex (A) and first and second sides (12A, 12B) extending from the apex. The central section may include detachable sections that are modular and removable from one another. The central section (12) may be flexible (either inherently or by incorporating flexible regions into the body of the central section). In this regard, the central section may be described as a flexible arch with dimensions that can be customized for a desired flexibility and elasticity (i.e., regions of the tissue bridge may be made thicker or thinner as necessary). Respective first and second lateral sections (11A, 11B) extend from the first and second sides (12A, 12B). The embodiment of FIGS. 1 and 8 show respective transition regions (19A, 19B) between the central section and the lateral sections. FIG. 1 shows that the tissue bridge (10) is originally manufactured with a predefined at-rest separation distance (D1) between the first and second sides (12A, 12B) and a predefined at-rest separation distance (L1) between each lateral section (11A, 11B). As used herein, the term "at rest" is used in the ordinary sense in that a manufactured tissue bridge (10) has a natural shape and state in which it lies "at rest" before any outside forces act upon it.

In one embodiment, the tissue bridge is made of a polymer that allows for deforming the tissue bridge (10) to load potential forces into the structure before applying the device to the tissue plane (5). The polymeric nature of the tissue bridge (10) provides sufficient elasticity to the overall structure such that the tissue bridge (10) tends to return, or at least tries to return, to its original shape after deformation. Holding the tissue bridge (10) in a deformed position, therefore, "loads" the tissue bridge with potential energy. By applying the tissue bridge (10) to the tissue plane (5) in a force loaded state (i.e., by deforming the structure and holding the deformation until application), the tissue bridge (10) releases particularly directed forces onto the tissue plane (5) in a resultant vector that has been previously planned and engineered to bring about a desired result. The deformation of the tissue bridge (10) may be calculated and precisely defined in terms of changes to the tissue bridge structure so that the tissue bridge exerts particular resultant forces on a tissue plane when the user attaches the tissue bridge to the patient. The elastic nature of the tissue bridge also gives the device a dynamic quality that moves with the tissue as healing or other activity occurs along a treatment area. The tissue bridge disclosed herein is sufficiently pliable to adjust itself to either a patient's own body movements or to accommodate incremental adjustments occurring in a tissue plane over time. The central section, the transitional zones or shoulders, and the lateral sections may have particularly engineered moduli of elasticity, which may be symmetrical or asymmetrical. The device may be of a single piece construction or may include parts that are detachable from each other.

FIGS. 7A to 7D show a representative series of schematic drawings in which a tissue bridge (FIG. 7A) has been distorted (FIG. 7B), applied to the tissue plane (FIG. 7C), and caused an eversion of tissue (5) across a treatment area (FIG. 7D). This is just one example of using a tissue bridge (10) to move the tissue within a tissue plane (5) to a desired state for healing (i.e., the eversion of tissue in FIG. 7D promotes healing and minimizing scar depression; removing tension across the treatment area (28) also reduces scarring overall). The movement of tissue is the result of the forces directed from the tissue bridge (10) onto the tissue plane (5). The resultant forces on the tissue plane are the direct result of deforming the tissue bridge prior to application to the patient; as the tissue bridge (10) reverts back from its deformed state toward its at-rest state, the tissue bridge moves the tissue in a pre-planned way.

Figure 3:
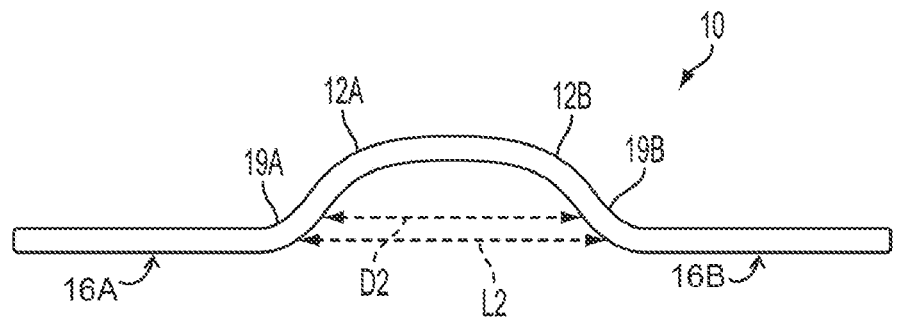
FIG. 3 shows a side elevation view of a tissue bridge pre-loaded with force as disclosed herein.

FIG. 1B provides a geometric summary of a tissue bridge used in accordance with the schematics of FIGS. 7A-7D. The resultant forces leading to the tissue configuration of FIG. 7D are accomplished by distorting the tissue bridge (10) prior to application onto the tissue plane (5). As shown in FIG. 3, this distortion includes separating the sides (12A, 12B) of the central section (12) of the tissue bridge (10) from an at-rest distance (D1) to a distorted distance (D2). From another perspective, the distortion, or pre-loading of the device, is accomplished by changing the distance between the lateral sections (11A, 11B) connected to the central section (12). Accordingly, the tissue bridge (10) includes a maximum distortion-induced separation distance (FIG. 3, D2) between the first and second sides (12A,12B) and a maximum distortion-induced separation distance (FIG. 3, L2) between the lateral sections of the tissue bridge (10).

The tissue bridge (10) directs forces, loaded into the device by deformation, onto a tissue plane (5) by connecting the tissue bridge (10) to the tissue plane (5) via respective attachment zones (16A, 16B) on the lateral sections (11A, 11B) (i.e., the underside of the lateral sections). When the lateral sections (11A, 11B) are affixed to the tissue plane, the first and second sides (12A, 12B) of the central section (12) are separated by a distance between the pre-defined at-rest separation distance (D1) and the maximum distortion-induced separation distance (D3). From another perspective, when the lateral sections (11A, 11B) are affixed to the tissue plane, the lateral sections are separated by a distance between the pre-defined at-rest separation distance (L1) and the maximum distortion-induced separation distance (L2).

Figure 4:
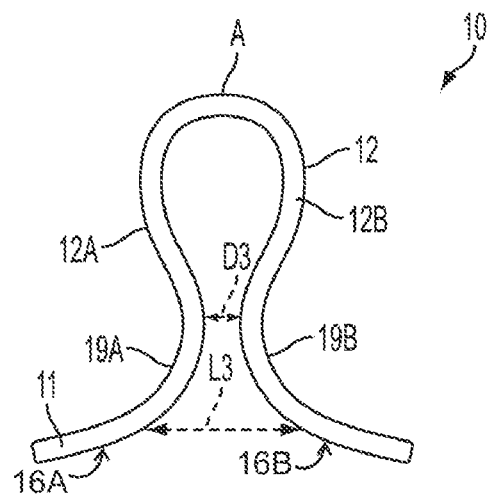
FIG. 4 shows a side elevation view of a tissue bridge in an at-rest position with compact sides facing each other.
Figure 5:
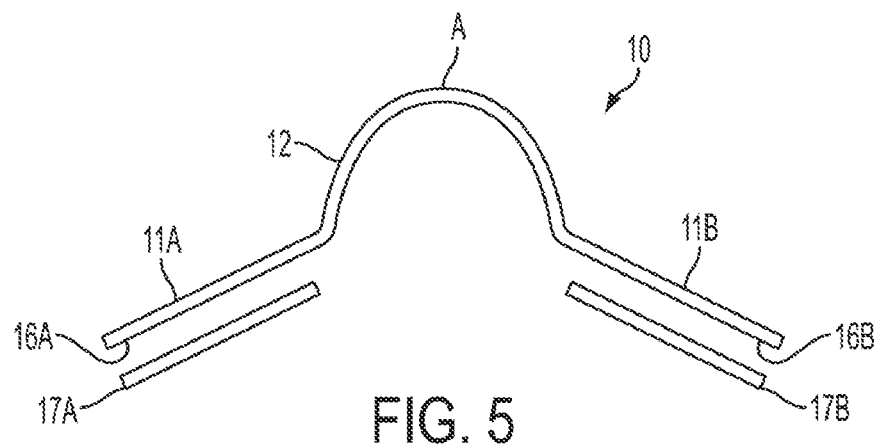
FIG. 5 illustrates a tissue bridge and adhesive combination as disclosed herein.

To illustrate another kind of resultant forces available from a tissue bridge, FIG. 4 shows an embodiment of the tissue bridge (10) which is in a closed position in an at-rest state. In this configuration, the dimensions between the sides of the central section (D3) and between the lateral sections (L3) are minimized during manufacture. Loading the device of FIG. 4, therefore, includes maximizing these distances prior to applying the device to the tissue plane (i.e., stretching the device apart). Upon application to the tissue plane, the device (10) tends to return to its at-rest, closed state and pulls sections of the tissue plane together.

Figure 9A:
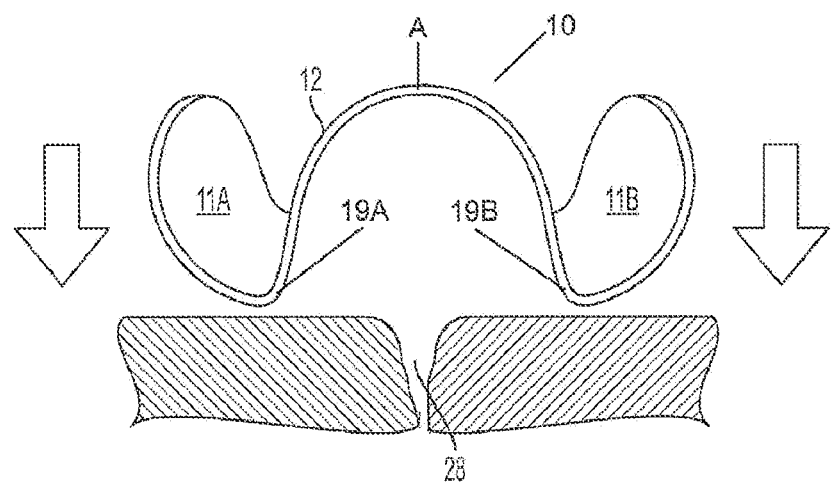
FIGS. 9A-9C illustrate the tissue bridge of FIG. 8 deformed for preloading force therein and applying a distracting force across a treatment area.
Figure 9B:
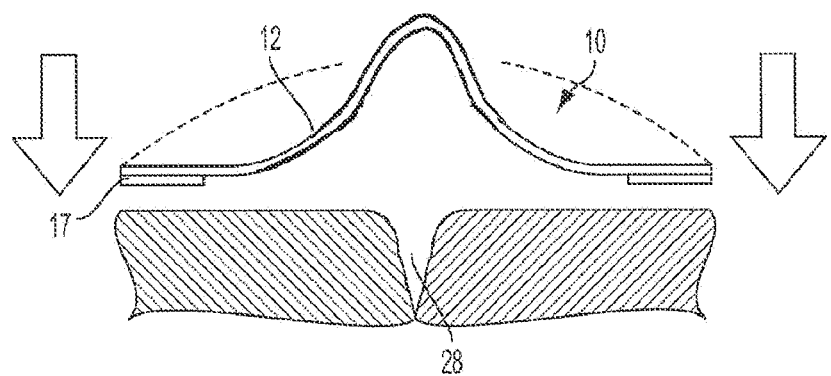
Figure 9C:
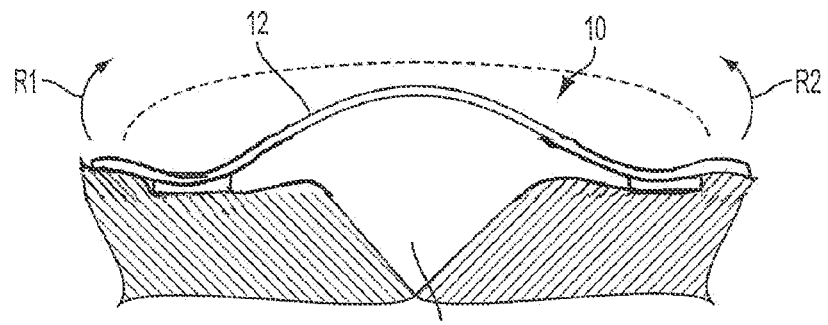

FIG. 8 illustrates yet another embodiment of the tissue bridge (10) and shows that the lateral sections (11A, 11B) may be configured at any angle relative to the central section (12). The tissue bridge of FIG. 8 is shown in FIGS. 9A-9C as being pre-loaded with forces that ultimately distract, or separate, a tissue plane (28). The lateral sections (11A, 11B) of the tissue bridge (10) may be manufactured in the upward direction pointing from a lower transitional shoulder (19) toward the apex (A) of the device. The device of FIG. 8 is loaded by bending the lateral sections downwardly toward a tissue plane (5) (FIG. 9B) and attaching the device (10) across a treatment area (28) via commonly used adhesives (17). As shown in FIG. 9C, the tissue bridge (10) has sufficient elasticity to move back toward its at-rest position after attachment to the tissue plane (5). The resultant forces (R1 and R2) from the tissue bridge (10) pull the tissue plane apart (i.e., present a distracting force across the treatment area (28) as shown in FIG. 9C).

The tissue bridge (10) and its application to a tissue plane (5) may be described according to the geometric construction of the device. Geometric terms are used only to describe the construction of the device and do not limit the invention in any way. For example, FIG. 1B and FIG. 8 illustrate the respective angles or arcs between component sections of the tissue bridge (10). In this regard, the tissue bridges of both FIG. 1B and FIG. 9 may be described as incorporating a central section (12) extending over a treatment area (28) on a patient. The tissue bridge (10) further includes respective first and second lateral sections (11A, 11B) joining the central section along respective connection segments (13), wherein the connection segments (13) lie within a common horizontal plane (H). As noted previously, the connection segments (13) and horizontal plane (H) are merely geometric references in space and do not limit the invention in any way. These terms are used to provide a geometric perspective rather than to show tangible pieces of the invention.

The lateral sections (11A, 11B) extend in an at-rest position at respective angles (Θ) from the horizontal plane (H). Respective attachment zones (16) on the lateral sections (11A, 11B) provide areas for connecting the lateral sections to the tissue plane (5).

From a geometric perspective, the tissue bridge (10) may be described as extending about a horizontal axis (x) and a vertical axis (y), both of which are non-limiting geometric references. The horizontal axis includes respective midpoints (M1, M2, M3) of the connection segments (13) between the lateral and central sections, as well as the midpoint of an imaginary geometric line segment connecting the lateral sections (11A, 11B). The vertical axis of the tissue bridge extends from an apex (A) of the central section (12) to the midpoint (M3) of the geometric line segment connecting the lateral sections. In this regard, the lateral sections of the tissue bridge (12) are represented according to the angle at which the lateral sections (11A, 11B) extend from the horizontal axis (x) of the tissue bridge (10). In the embodiment of FIG. 1B, the angle formed by the first lateral section (11A) and the horizontal axis (x) is between 180 and 270 degrees. The angle formed by the second lateral section (11B) and the horizontal axis (x) is between 270 and 360 degrees. References to degrees relate to the standard quadrant system for ease of reference.

The configuration of FIG. 8, however, shows a different arrangement that yields different resultant forces. In FIG. 8, the angle formed by the first lateral section (11A) and the horizontal axis (x) is between 90 and 180 degrees. The angle formed by the second lateral section (11B) and the horizontal axis (x) is between 0 and 90 degrees. The tissue bridge (10), therefore, may be constructed in an at-rest state with varying arrangements for connecting the lateral sections (11A, 11B) and the central section (12). The different angles at which the lateral sections extend, as noted of FIG. 1B and FIG. 8, provide distinctly different rotational forces to a tissue plane as evidenced by the different results shown in FIGS. 7D and 9C.

Figure 11:
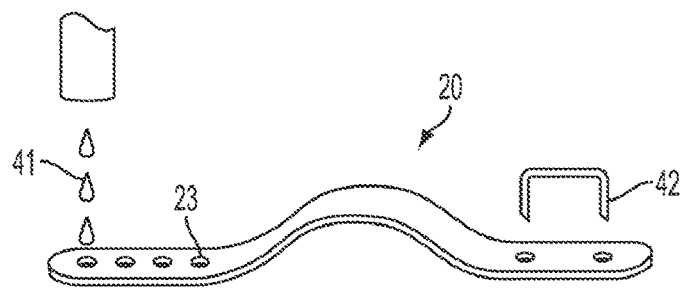
FIG. 11 illustrates numerous attachment mechanisms for applying a tissue bridge to a tissue plane in accordance with this invention.
Figure 12A:
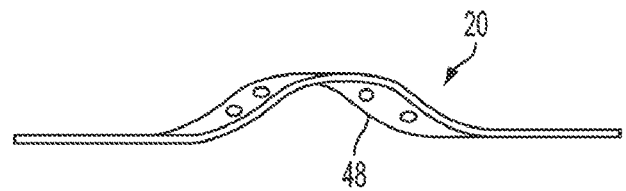
FIG. 12A illustrates a tissue bridge defining openings for medical access to a treatment area.
Figure 12B:
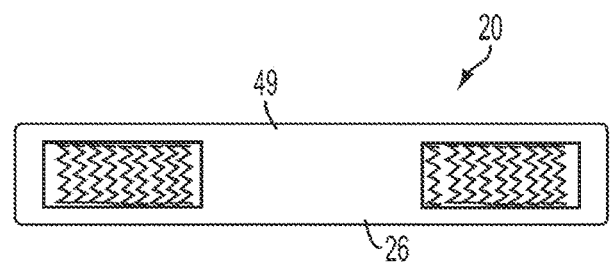
FIG. 12B illustrates a bottom plan view of a tissue bridge having adhesive layers thereon.

The tissue bridge (10) may be attached to a tissue plane (15) on a patient by many mechanisms. FIGS. 1 and 7A-7D illustrate that an adhesive layer (17) may be attached to an underside of each lateral section (11A, 11B) along attachment zones (16A, 16B). The adhesive layers (17) attach to the tissue plane. Other methods of attachment may be used, depending upon the environment in which the tissue bridge is applied. FIGS. 11 and 12 show that the tissue bridge may include openings (23) defined within the body of the tissue bridge to allow for liquid adhesives, staples, screws, and other mechanical fasteners to attach the tissue bridge to the tissue plane (5). Combinations of these attachment mechanisms may be used in certain specialized situations. As shown in FIG. 12B, the underside of the tissue bridge (10) may have grooves or striated sections for distributing adhesives across the entire underside of the tissue bridge (10) (i.e., a liquid adhesive placed on the underside of the device moves across the grooves for even distribution).

No matter which kind of attachment mechanism is used, the tissue bridge (10) is configured to apply forces across a tissue plane (5) and apply a medical treatment to the area under the tissue bridge. The kinds of treatment available by using the tissue bridge include, but are not limited to (i) reducing tension across the treatment area with forces directed from said lateral sections toward said central section, (ii) compressing the treatment area; (iii) approximating sections of the tissue plane across the treatment area; (iv) aligning sections of the tissue plane across the treatment area; (vi) fixation of tissue; and (vii) modulating forces across the wound.

Figure 10A:
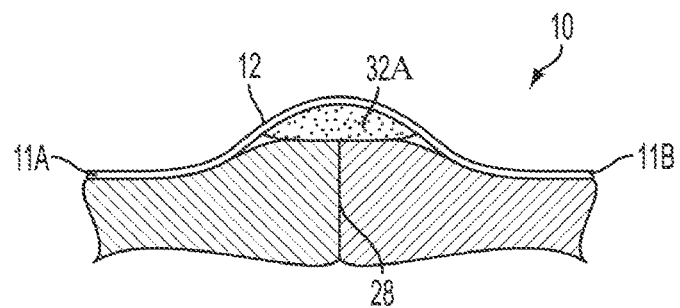
FIGS. 10A-10C illustrate accessories that may be used in combination with a tissue bridge in accordance with the invention disclosed herein.
Figure 10B:
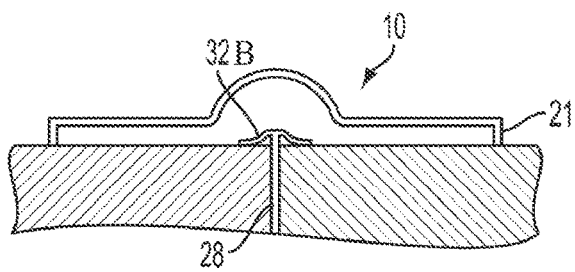
Figure 10C:
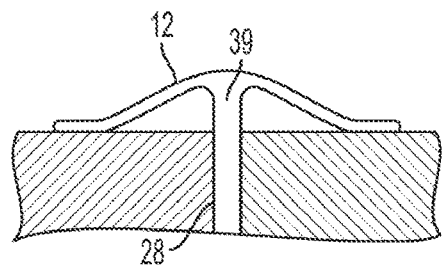

The tissue bridge (10) may also be used in combination with other tools that are useful for medical intervention across a treatment area. FIGS. 10A-10C illustrate that the tissue bridge (10) accommodates a pad (32A) which may dispense additional medicine (e.g., antibiotics, wound healing medications, anesthesia) or provide an absorptive surface (e.g., gauze). FIG. 10B illustrates that the tissue bridge (10) may serve as a protective shield to cover a tissue plane when an implanted device (32B) extends into the tissue plane and requires protection. The tissue bridge (10), therefore, may be used on tissue that includes an incision or a wound or merely requires protection without touching the tissue. Along these lines, the tissue bridge (10) may incorporate a central section (12) that includes an extension (39) that serves as a guide to direct the user in positioning the central section (12) to a particular point on the tissue plane. In this regard, the extension (39) may be placed onto the tissue plane (5) prior to affixing the tissue bridge (10). Alternatively, the extension (39) may be place within an incision or opening of the treatment area (28), particularly along one side of an opening in the tissue plane, before affixing the tissue bridge (10) and pulling the treatment area (28) into a closed position. FIG. 12A shows that the central section (12) may define openings (26) allowing the user to access the treatment area from the top of the device. The openings (26) may allow for medical treatments such as the application of liquid medications through the openings (26).

Figure 13A:
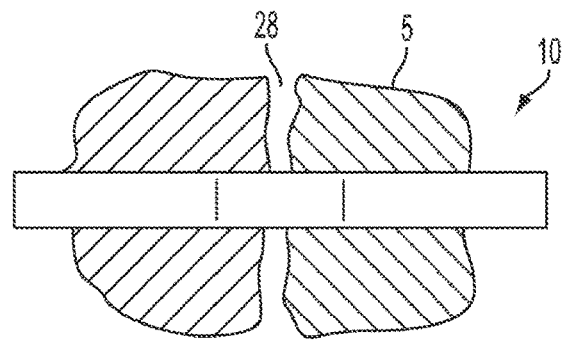
FIGS. 13A-13D illustrate use of a tissue bridge either alone or in combination over a treatment area.
Figure 13B:
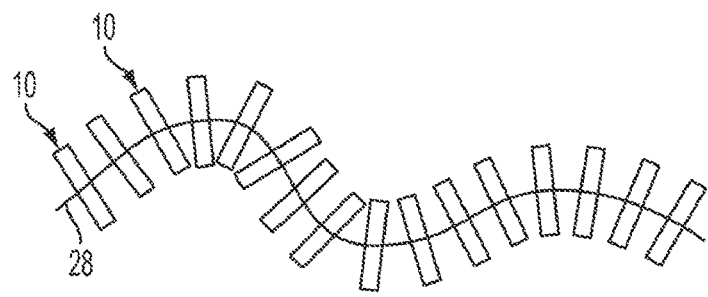

The tissue bridge may be used as a stand-alone device as shown in FIGS. 7, 9, and 13A. In different embodiments, shown schematically in FIGS. 13B, 13C, and 13D, multiple tissue bridges are applied in series across a tissue plane (5) for medical treatment. The multiple tissue bridges may be linked by a common connector that may also serve a medical purpose such as occluding a wound or other treatment area. FIG. 13B illustrates that the tissue bridge (10) may be used as part of a system in which the specialized forces directed onto a treatment area (28) are engineered to treat an entire section of a tissue plane. In the example of FIG. 13B, the section includes a contoured incision or opening in the tissue plane, and the tissue bridges (10) are placed along the contour in a strategic configuration to promote wound healing with less scarring.

Figure 13C:
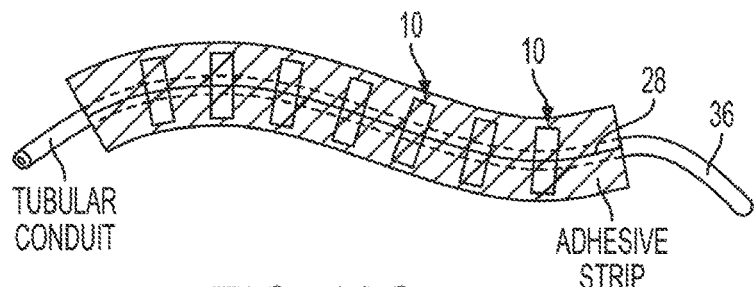
Figure 13D:
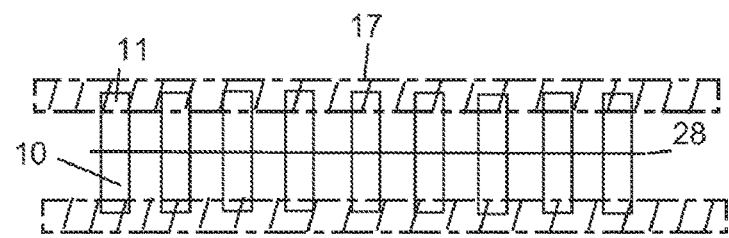

FIG. 13C illustrates a different kind of system for medical treatment in which a series of tissue bridges (10) serve as scaffolding for creating an open space between a treatment area (28) and the central section of the tissue bridge (10). The curvature or raised nature of the tissue bridge central section provides a protective space over the treatment area. The open space formed through a series of tissue bridges may form a channel through which medical intervention is accessible. FIG. 13C illustrates that the scaffolding presented by a series of tissue bridges (10) may also serve to hold up an applied sheet (43) or layer of material that further protects the treatment area (28). An applied sheet (e.g., a polymeric adhesive sheet) allows the user to establish a covered channel between the applied sheet (43) and the treatment area (28) for medical intervention. For example, a pump may be attached to the covered channel for draining the treatment area (28), irrigating the treatment area (28), or applying suction to the treatment area (28). Of course, the applied sheet or adhesive would have the structural stability to withstand such uses (i.e., upon applying suction and creating a vacuum under the sheet, the sheet would not collapse). The embodiment of FIG. 13C further shows that a separate conduit (36) may fit within the covered channel. The separate conduit (36) may be tubing that applies medication or accomplishes another goal such as irrigating or draining a wound. With a covered channel extending across a treatment area (28) and serving as a region of medical intervention, the tissue bridges (10) may be applied to a tissue plane (5) with a secondary adhesive (41) to ensure proper stability.

Figure 14A:
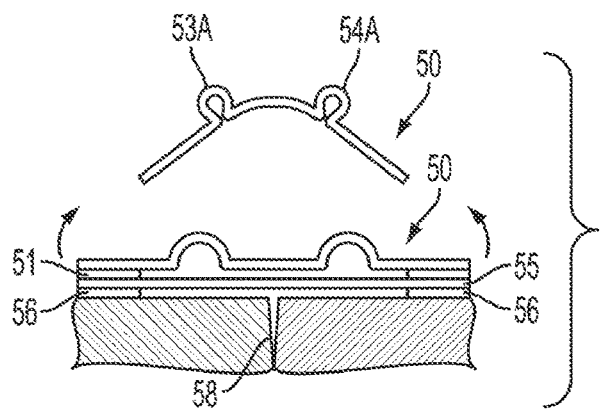
FIGS. 14A-14D illustrate tissue bridges having multiple expanders across a central section.
Figure 14B:
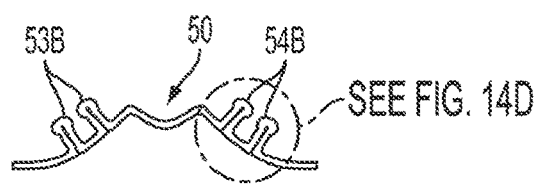
Figure 14C:
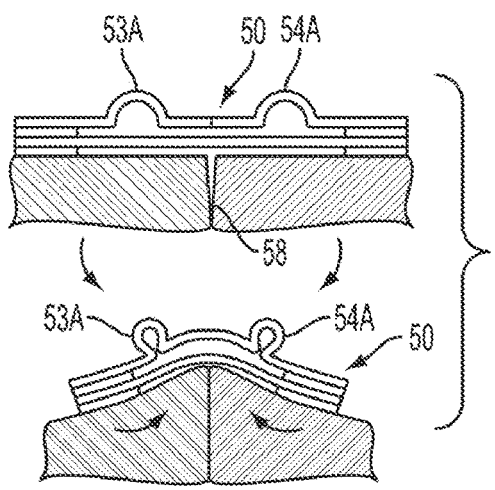
Figure 14D:
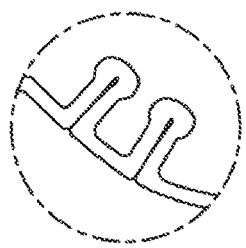

Whether a tissue bridge (10) is used as a stand-alone device (FIGS. 7, 9, 13A) or in combination (FIGS. 13B-13D), the shape of the tissue bridge (10) and the way that it deforms during loading are customizable for each application at hand. For example, FIGS. 14A, 14B, and 14C show that the central section may include additional portions (53a, 54a) that are deformable to load the tissue bridge (50) with potential energy to be distributed over the treatment area (58). In the upper portion of FIG. 14A, a tissue bridge (50) exists in an at-rest position prior to deformation. Upon deforming this "double loop" embodiment, the deformable portions (53a, 54a) expand and lateral portions attach to a treatment area (58) via adhesive sections (51). As in other embodiments disclosed above, the tissue bridge (50) is designed for direct attachment to a patient via adhesive sections (51). The embodiment illustrated in FIG. 14, however, incorporates a separate bandage (55) between adhesive sections (51) on the tissue bridge (50) and the treatment area (58). FIG. 14C shows that upon application to the treatment area, the tissue bridge (50) reverts back toward its at-rest shape and state (FIG. 14A). The compressive forces pulling the tissue together along the treatment area (58) are illustrated in FIG. 14C by the arrows within the tissue plane and pointing toward the treatment area (58).

The "double loop" embodiment of FIG. 14 is one example showing how the overall concept of a tissue bridge encompasses various embodiments in which the shape of the device is engineered to produce a particular set of resultant forces on a tissue plane. The regions of the tissue bridge which are deformed to pre-load energy and force potential into the device may take any size and shape. These deformable areas may also be formed of any kind of material that produces force vectors within a desirable range of magnitudes and directions. While FIG. 14A shows two expandable regions, or loops (53A, 54A), across a central section, FIG. 14B illustrates that even the deformable loops themselves may be configured in various shapes and sizes, such as the compressed expanders (53B, 54B) shown in FIG. 14B. The compressed expanders (53B, 54B) are significantly more linear, as opposed to the arched configuration of FIG. 14A, and the sides of each expander (53B, 54B) are manufactured to lie closer to one another in an at-rest state. The different configurations for the respective expanders allow for customizing the resultant forces from each tissue bridge. FIGS. 14A and 14B show that by engineering the central and lateral sections of a tissue bridge with customized shapes formed in suitable materials, the tissue bridge can generate numerous forces of particular magnitude and direction desired for placement onto a tissue plane.

FIG. 14 also shows that a single tissue bridge (50) may incorporate multiple expanders (53A, 53B, 54A, 54B) along a single piece body to increase the magnitude of potential energy pre-loaded into the device. By forming a tissue bridge with a plurality of expanders (53A, 53B, 54A, 54B), the device generates a resultant force vector of altered magnitude in relation to the height of the expander as compared to a tissue bridge that utilizes only one expander of the same size. In fact, the tissue bridge (50) shown in FIG. 14 allows for the height of each expander (as measured from the above-noted horizontal axis (x)) to be minimized, thereby creating a lower profile for the tissue bridge on the tissue plane. In other words, the "double loop" embodiment shown in FIG. 14 generates a resultant force that would otherwise be achieved with a much larger central section (i.e., a single expander device would require an increased height of the central section as measured from the horizontal axis (x)).

The tissue bridge (10) disclosed herein is adaptable for use with numerous attachments and secondary instruments to ensure efficient deformation and force loading as well as placement on a patient. FIGS. 15-18 illustrate examples of the accessories that may be incorporated into a system that uses a tissue bridge to promote wound healing. These Figures are included only as examples and are not limiting of the invention in any way.

Figure 15:
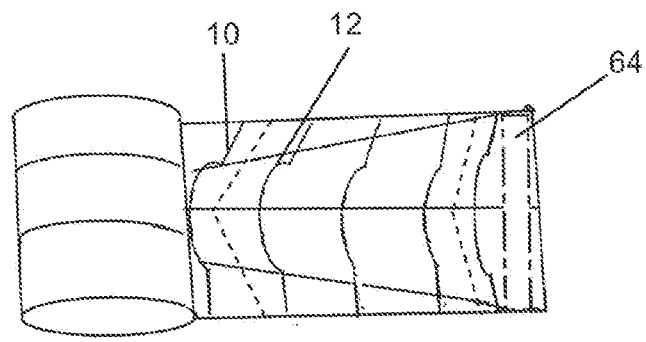
FIG. 15 illustrates a tissue bridge dispenser and applicator for use with a tissue bridge as disclosed herein.

FIG. 15 illustrates that tissue bridges may be incorporated into a dispenser (60) that holds a multitude of individual tissue bridges (D). The embodiment of FIG. 15 shows that the tissue bridges are distributed from an opening (64) within the dispenser (60) via a roll of tape or other adhesive (R). The dispenser (60) is configured to move the tissue bridges (D) out of the dispenser along a channel having a sloped dimension that presses onto the central section (12) of a tissue bridge to pre-load the tissue bridge for direct application onto a patient. The dispenser of FIG. 15 is just one example of a dispenser that stores a multitude of tissue bridges, dispenses the tissue bridges, and serves as a direct applicator of a pre-loaded tissue bridge onto a treatment area.

Figure 16A:
FIGS. 16A and 16B illustrate an accessory for manual loading of a tissue bridge as disclosed herein.
Figure 16B:
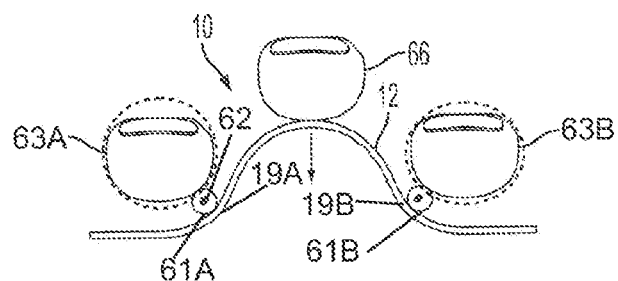

FIGS. 16A and 16B are additional examples of how tissue bridges (10) disclosed herein may incorporate additional features allowing for convenient application of a tissue bridge (10) onto a patient's treatment area. FIG. 16A shows a specialized kind of ring (63) that a user may wear on respective fingers as illustrated in FIG. 16B. The rings (63A, 63B) each include attachment projections (62) extending from the respective bodies of the rings such that the projections are parallel to the user's fingers when worn. The tissue bridge connectors (61A, 61B) are shown in more detail in FIG. 16B and, in one example, are proximate to a transitional shoulder (19A, 19B), which may be arcuate or angled in construction and include regions of varying or customized thickness. A user may access the connectors (61A, 61B) manually or with a secondary instrument to load the tissue bridge (10) by expanding the central section (12). In the example of FIG. 16, the connectors (61A, 61B) may be accessed with attachment rings (63A, 63B) worn on a user's two nonadjacent fingers. The user connects the rings (63A,63B) to the connectors (61A, 61B) for conveniently expanding the central section (12) via the transitional shoulders (19A, 19B) while simultaneously pressing down on the apex (A) of the central section (12). Instead of pressing down onto the central section manually, the user may also choose to employ a plunger (65) shown in FIG. 17A to press down and expand the central region 12. The embodiment of FIGS. 15-17 present examples of ways in which manual loading of potential force into the tissue bridge is more efficiently accomplished with customized accessories. Accordingly, the tissue bridge may be included with a kit of secondary instruments that aid in using the tissue bridge.

Figure 17A:
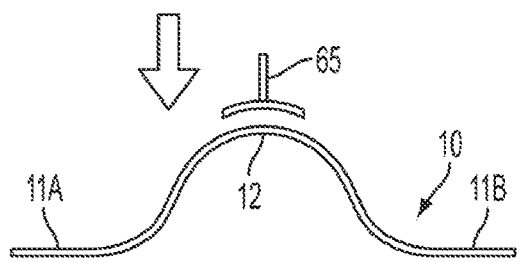
FIGS. 17A-17D illustrate embodiments of tissue bridges as disclosed herein in use with secondary devices for pre-loading the tissue bridge with potential force.
Figure 17B:
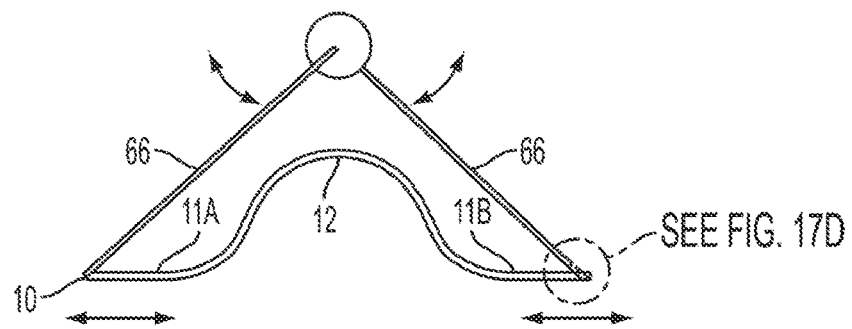
Figure 17C:
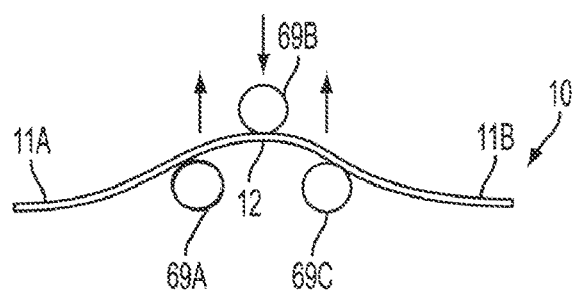
Figure 17D:
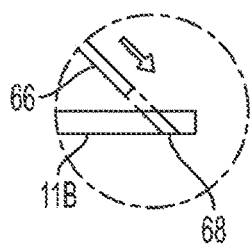

The above noted kit of secondary instruments for use with the tissue bridge may also include a lateral expander (66) shown in FIG. 17B. The lateral expander (66) allows for the tissue bridge (10) to be loaded via the lateral sections (11A, 11B) by connecting the lateral expander (66) to the respective lateral sections (11A, 11B). In one embodiment, the lateral expander (66) has a shape and associated dimensions that mate with a groove, passageway, or other lateral section attachment point (68) to facilitate deforming the device and preloading potential force therein. FIG. 17C illustrates that a hand held deforming mechanism (69) (e.g., a crimper) may include projections (69a, 69b, 69c) that fit on opposite sides of a tissue bridge (10) to expand the tissue bridge. The shape of the crimper pins may be altered or customized to suit a particular tissue bridge shape.

Figure 18A:
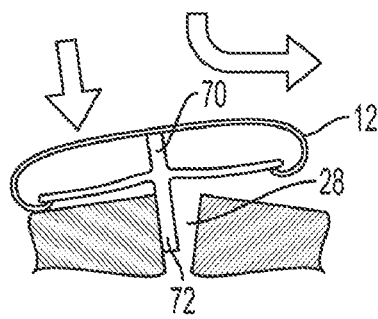
FIGS. 18A-18C illustrate use of a tissue bridge according to this invention and utilizing a guide stem for placement into a treatment area.
Figure 18B:
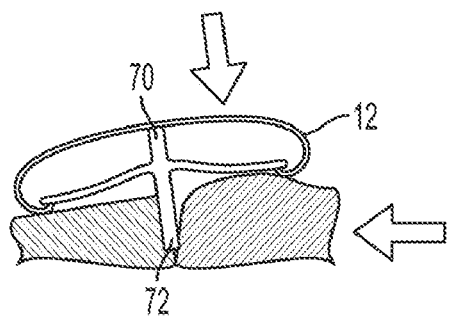
Figure 18C:
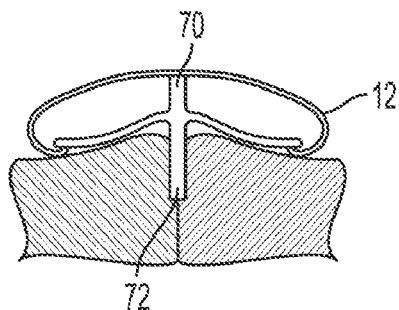

In addition to secondary instruments that pre-load a tissue bridge (10), the tissue bridge may also be associated with devices that assist in placement of a tissue bridge. For example, the body of a tissue bridge (10) may include measurements, markings, scales, or other visual indicators useful in measuring a precise placement for the tissue bridge (10) onto the tissue plane (5). The tissue bridge may also accommodate a guide stem (72A) that includes laterally extending stabilizing arms (72B) attaching to lateral sections (11A, 11B) of a tissue bridge (10). The guide stem (72A) is shown in FIG. 18A as being useful for placing against one side of a treatment area (28) to facilitate bringing an opposite side of the treatment area into alignment with the guide stem (72A) (FIGS. 18B, 18C). Generally, FIGS. 17B, 17C, and 18 show exemplary embodiments of secondary instruments that may be used to load the tissue bridge from points on the outer ends of the device instead of operating only on the central section (12).

Figure 19A:
FIGS. 19A-19V illustrate numerous shapes and configurations of both the central sections and the lateral sections of tissue bridges according to this disclosure.
Figure 19B:
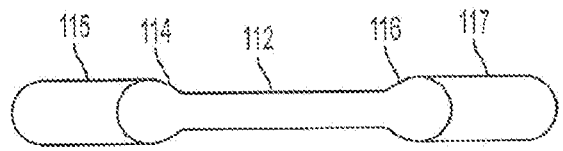
Figure 19C:
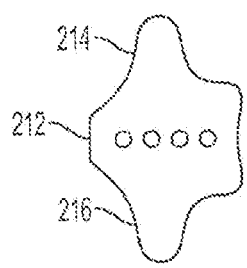
Figure 19D:
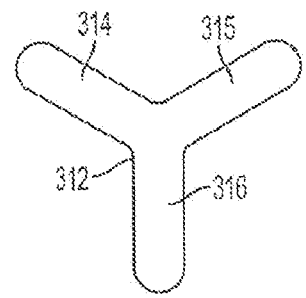
Figure 19E:
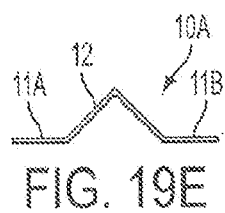
Figure 19F:
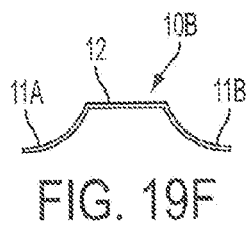
Figure 19G:
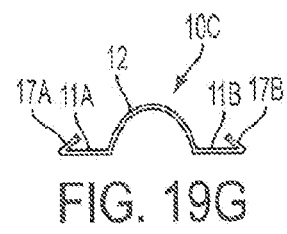
Figure 19H:
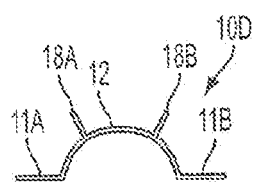
Figure 19I:
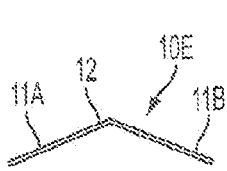
Figure 19J:
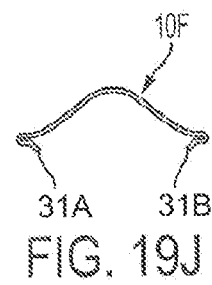
Figure 19K:
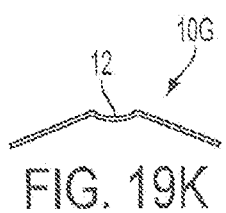
Figure 19L:
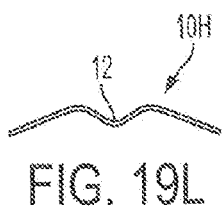
Figure 19M:
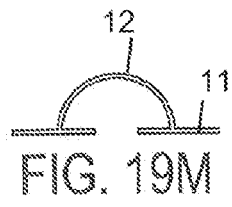
Figure 19N:
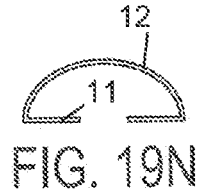
Figure 19O:
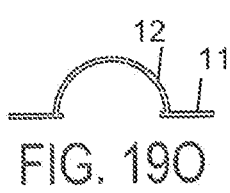

The tissue bridge (10) accommodates any shape and size necessary for producing a desired resultant force in a particular direction on a tissue plane (5). FIG. 19 of this disclosure shows over twenty proposed shapes and configurations for the lateral sections (11A, 11B), the central sections (12), and the transitional sections (19) that may be included in any tissue bridge (10). FIG. 19A shows a top view of a tissue bridge and includes a narrowing yoke across the uppermost portion of the central section (112) and expands the width of the lateral sections (114, 116) for a customized embodiment. FIG. 19B expands the narrowing yoke lengthwise along the central section (112), rounds the lateral sections (114, 116) and uses adhesive tabs (115,117) extending from the lateral sections for attaching the tissue bridge to the tissue plane. FIG. 19C illustrates significantly modified and customizable shapes for a top view of the subject tissue bridge (214). FIG. 19D shows that a tissue bridge (312) may include more than one lateral section (314, 315, 316) to apply particularly directed forces across a greater surface area on a tissue plane or to generate converging forces from multiple directions. FIGS. 19E-19O illustrate respective cross sections of various tissue bridges that are possible by manufacturing the tissue bridge as a single piece instrument with uniquely engineered portions that provide an appropriate set of resultant forces. In particular, FIG. 19G includes lateral folds (17A, 17B) to accommodate an applicator. FIG. 19H includes handles (18A, 18B) for manually expanding the tissue bridge about a vertical axis. FIG. 19J attaches the tissue bridge to a tissue plane via prongs (31A, 31B), which are also useful for attaching adhesive sheets as shown in other embodiments of this invention such as FIG. 29. FIGS. 19M through 19O illustrate that different resultant forces may be achieved by attaching the central section and the transitional shoulders at different points along a face of the lateral sections. FIGS. 19P-19V show increasingly specialized kinds of tissue bridges in which the shape produces a desired resultant force. In FIG. 19P, the shape of the lateral sections (11) are asymmetrical so that different regions of a treatment area (28) are affected by different resultant force vectors. FIGS. 19Q and 19R indicate that the central region (12) may be round with the lateral sections extending radially to close circular incisions or other wounds that benefit from resultant forces emanating all around the treatment area. FIG. 19S illustrates that the lateral sections (11) may be of any number and any combination of shapes, depending upon the area of the tissue plane on which the lateral section will be placed. FIGS. 19T and 19V provide symmetrical force vectors on either side of a treatment area whether attached with adhesive directly under the tissue bridge (19T) or with an adhesive strip extending over the lateral sections (19V). FIG. 19 U shows that the tissue bridge (10) may be any simple shape (e.g., a rectangle) and define an opening of proper dimensions to adjust the resultant forces on the tissue plane.

FIGS. 20-29 expand the concept of a tissue bridge into areas of medicine that require specialized ways of applying the tissue bridge, varying degrees of symmetry across the structure of the tissue bridge, and accessories that promote using the tissue bridge on tissue planes that may not be homogenous (i.e., a tissue plane that has a bone portion and a muscle portion with different requirements for attachment). For example, FIG. 20 illustrates that the tissue bridge (10) may be used with an applicator (80) that defines an opening (82) for receiving the central section (12) of the tissue bridge. Edges of the applicator (80) surrounding the opening (82) attach to the tissue bridge (10), and this attachment may be temporary or permanent. The applicator (80) of FIG. 20A is just one example of the shape and orientation of an applicator for the tissue bridge and includes a folding region (84) along its midsection for angular movement of opposing sections of the applicator (80). By bending the applicator (80) along the folding region (84) the attached tissue bridge deforms in either direction to pre-load potential force into the tissue bridge (10). FIG. 20C shows a top perspective of a loaded tissue bridge with the applicator (80) still in place after deforming the tissue bridge. The embodiment of FIG. 20C is ready for placement across a tissue plane (not shown).

FIG. 21 illustrates several examples of tissue bridges manufactured with multi-piece assemblies connected by moveable joints or hinges (14A, 14B). FIG. 21 includes embodiments in which structural features of the tissue bridge (10) are connected in varying configurations to achieve different purposes on a tissue plane. For example, similar to FIGS. 19M, 19N, and 19O, FIGS. 21A-21D shows that the central section (12) may be connected to the lateral sections (11A, 11B) at different points along a face of the lateral sections (i.e., FIG. 21A attaches the central section at the midpoint of the lateral section, FIG. 21B connects at a medial area of the lateral sections, and FIG. 21C connects at the outer ends of the lateral sections. Each of the configurations shown in FIG. 21 includes the hinged assemblies (14A, 14B) so that the angle of rotation for the tissue bridge is adjustable by moving the lateral sections up and down. The hinges (14A, 14B) may include a ratcheting function that holds the hinged assembly in place at a desired angle. FIG. 21D further incorporates a rotation function via a joint (14C) at the apex of the central section (12). The rotatable joint (14C) provides a mechanism for further customization of the device to fit along a tissue plane that is non-linear.

Figure 22A:
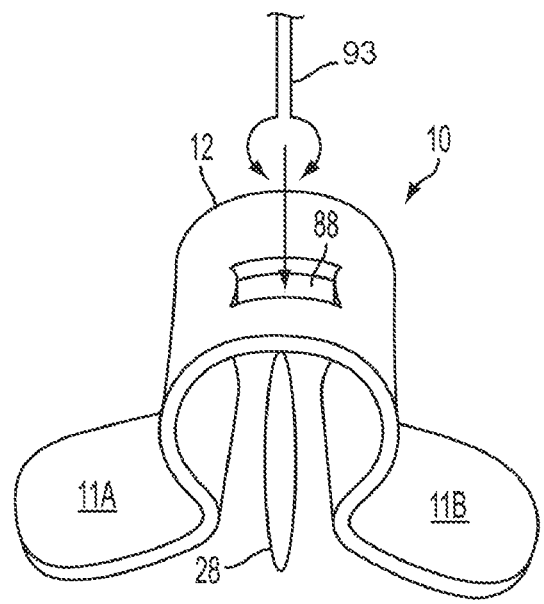
Figure 22B:
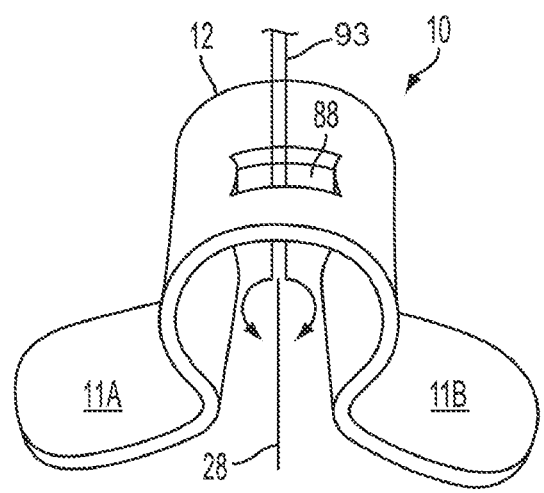

In yet another embodiment of secondary instruments used with the tissue bridge disclosed herein, FIG. 22 shows that the central section (12) of the tissue bridge (10) may define a central section opening (88) through which a user accomplishes medical intervention on a treatment area (28). The opening (88) is available for visual inspection, application of medicines, or for inserting another tool, such as the clamp (93) shown in FIG. 22. FIG. 21A illustrates that the user may insert the clamp (93) through the opening (88) and pull a tissue plane together across the treatment area (28) as shown in FIG. 22B. The clamp (93) may be inserted to align tissues either before the tissue bridge is preloaded, during the period that it is preloaded, or even after the tissue bridge is loaded with potential force. In one example, the clamp (93), may bring tissues into approximation before the preloaded bridge is attached to the tissues, thus facilitating both alignment and centering of the tissue bridge over the treatment area.

Figure 23A:
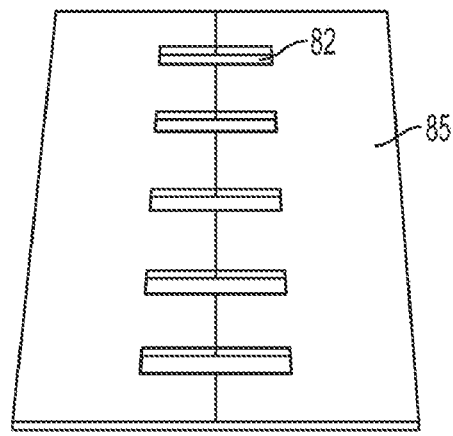
FIGS. 23A-23B illustrate a tissue bridge applicator as set forth in FIG. 20 that accommodates preloading and applying multiple tissue bridges onto a treatment plane.
Figure 23B:
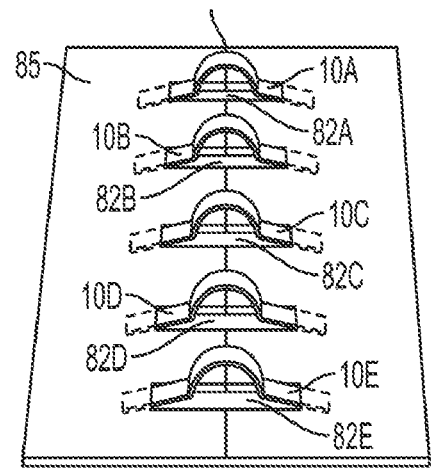

The tissue bridge disclosed as a stand-alone device in FIG. 1 may be used in combination as shown in FIG. 13B. In this way, a series of tissue bridges (10) traverse a treatment area and provide resultant forces along a path defined by the user. The tissue bridges may be pre-loaded to apply varying degrees of force at magnitudes and directions engineered to produce a desired result at distinct points along the treatment area. Along those lines, the tissue bridge applicator of FIG. 20 may be manufactured to accommodate multiple tissue bridges as shown in FIGS. 23A and 23B. The applicator (85) defines numerous applicator openings (82A-82E) so that the tissue bridges (10A-10E) connect to the applicator for simultaneous loading and attachment to a tissue plane. By bending the applicator (85) along a folding area (87), an attached tissue bridge (10A-10E) is deformed and loaded with potential force. In one embodiment, the applicator peels away from the tissue bridges after application to a tissue plane. In other embodiments, the applicator may remain in place for additional protection at the option of the user.

The tissue bridge applicator (85) shown in FIG. 23A may actually be used to bridge forces along a tissue plane via a stretchable sheet or bandage (90). In this embodiment, the tissue bridge applicator (85) operates without the stand alone tissue bridges (10A-10E) and applies, instead, the flexible sheet (90) across a treatment area. In this regard, the tissue bridge applicator (85) and the flexible sheet (90) are essentially a "two part" tissue bridge with the elastic function of the bridge provided by an elastic element (90), and the non-compressibility, rigid characteristic of the bridge being provided by the applicator (85). This embodiment essentially shows a composite tissue bridge that is applied as a two-piece bridge, and as the tissue plane heals (i.e., swelling reduces), the tissue bridge applicator (85) may be removed, leaving behind the flexible sheet.

Figure 24:
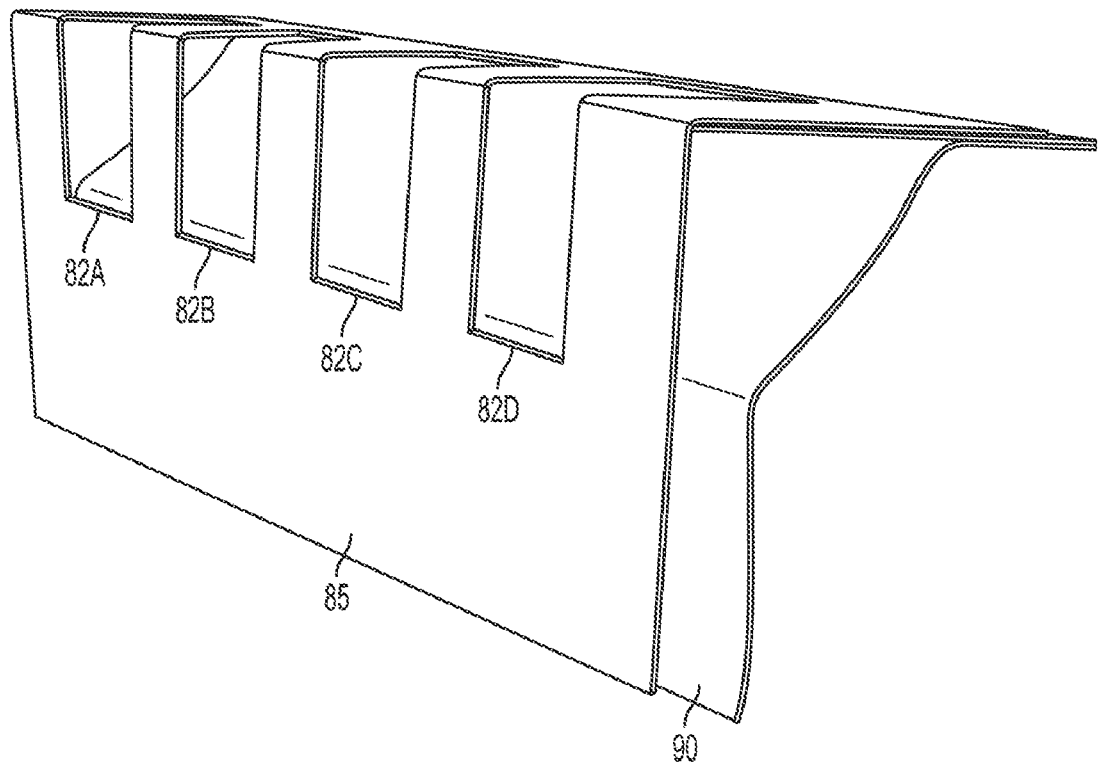
FIG. 24 illustrates a composite tissue bridge including a removable applicator and a flexible sheet providing tension along a treatment area.
Figure 25A:
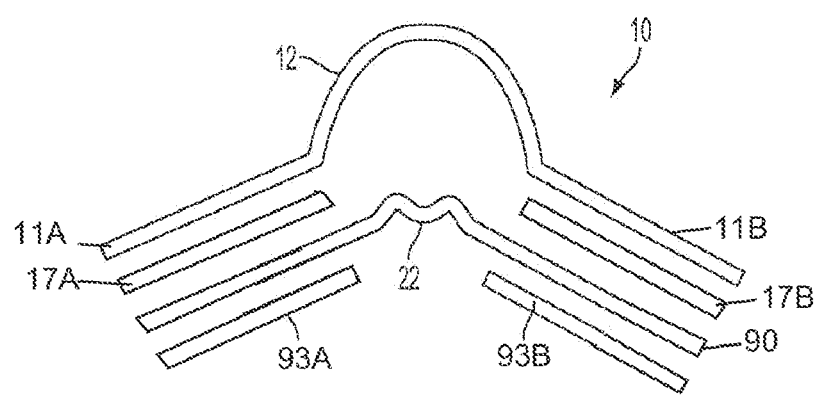
FIGS. 25A-25B illustrate a tissue bridge as set forth herein and attaching a flexible sheet via appropriate adhesives to a treatment area.
Figure 25B:
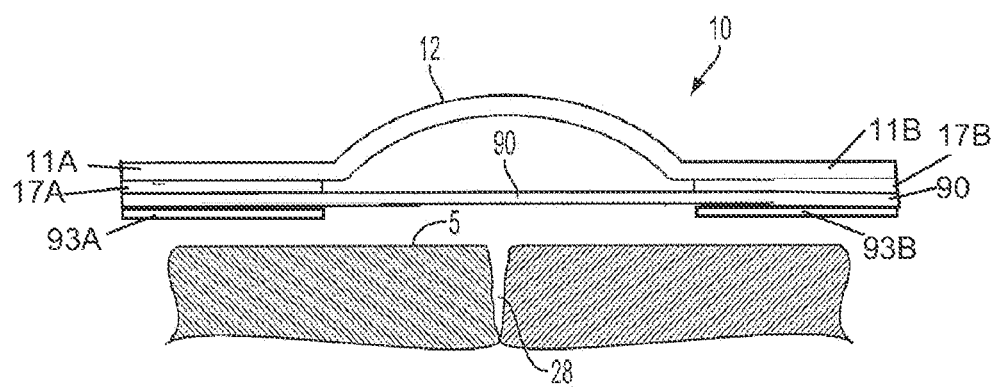
Figure 26A:
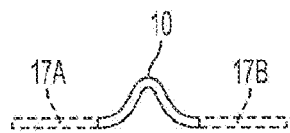
FIGS. 26A-26F illustrate various combinations of a tissue bridge with adhesives and other bandaging.
Figure 26B:
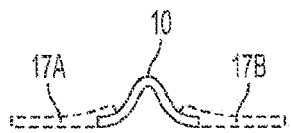
Figure 26C:
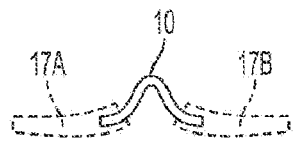
Figure 26D:
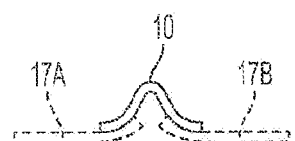
Figure 26E:
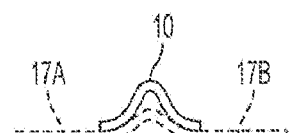
Figure 26F:
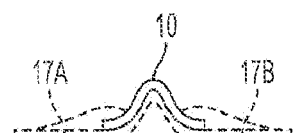

This embodiment of the invention allows for the flexible sheet (90) and the tissue bridge applicator (85) to be manufactured and shipped in a folded arrangement with neither the applicator (85) nor the sheet (90) under the stress of tension. This is useful because the flexible sheet (90) may be a bandage, an adhesive, or another kind of sheet formed of a polymer that deforms and breaks down over time when under constant stress. The folding embodiment of FIG. 24 illustrates one way in which a tissue bridge applicator and associated sheet accomplish the functions of a tissue bridge by connecting the sheet across a treatment area. By unfolding the applicator (85), the user stretches the sheet (90) to a pre-engineered level of tension. Placing the sheet over the treatment area causes the sheet (90) to revert back to its at-rest state prior to unfolding and placing resultant forces across the treatment area (i.e., a stretched sheet applied to the tissue plane will pull inwardly). The flexible sheet (90) may be attached to the tissue plane by known adhesives, either permanent or temporary. FIGS. 25A and 25B illustrate that a similar bandage application may be accomplished with the stand alone tissue bridge (10) connected to a bandage (90). FIG. 25A indicates a slack, or tension free, region (22) within the flexible sheet (90) that allows for the tissue bridge (10) to be pre-loaded by deforming the central section (12) and the lateral sections (11), while simultaneously extending the flexible sheet (90). FIG. 25B shows the embodiment of FIG. 25A with a pre-loaded tissue bridge (10) extending the flexible sheet (90) for placement onto a treatment area (28) with appropriate adhesive layers (17, 93).

Figure 27A:
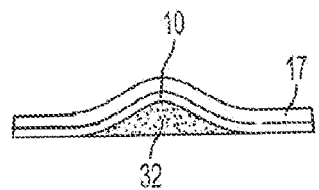
FIGS. 27A-27B illustrate a tissue bridge used in conjunction with padding and an adhesive sheet.
Figure 27B:
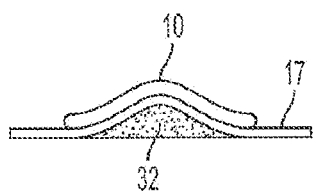

Embodiments combining a tissue bridge (10) with a bandage or with bandaging functions add yet another dimension to the utility of the tissue bridge concept. The tissue bridge (10) may be used to place a bandage, an absorptive sheet, a protective cover, or an adhesive layer over a treatment area for medical intervention onto the tissue plane (5). In this regard, the tissue bridge (10) may be formed integrally with a bandage or other sheet that adheres to a tissue plane. FIGS. 26A-26F illustrate this concept by showing the tissue bridge (10) formed with attached adhesive layers (17A, 17B). The adhesive layers (17A, 17B) are not limiting of the invention but are mere examples of the kinds of sheets that can be used with a tissue bridge so that the entire combination is used to treat a patient. Embodiments showing the adhesive layers (17A, 17B) connected to lateral sections (11A, 11B) provide a means for deforming the tissue bridge (10) by peeling a backing off of the adhesive layers (17A, 17B). Other embodiments (FIGS. 26E, 26F) illustrate that the tissue bridge may be used to apply the adhesive sheet onto the treatment area with the adhesive sheet (17A, 17B) encompassing the entire footprint of the tissue bridge. FIGS. 27A and 27B illustrate that the sheets used in combination with a tissue bridge may be medicinal layers, adhesive layers, tensioning sheets, or other layers of material used to direct force or other medical intervention onto a tissue plane. The tissue bridge may be between these layers (FIG. 27A) or may be attached over the layers (FIG. 27B).

Figure 28:
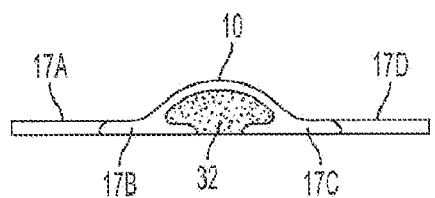
FIG. 28 illustrates a tissue bridge according to this disclosure incorporating sections of adhesive layers having varying strength and removability along a tissue plane.

FIG. 28 incorporates a padding layer (32) to a central section (12) of the tissue bridge (10). The padding layer (32) may deliver medications, absorb fluid, or merely provide comfort to a painful or sensitive area on a tissue plane. The lateral sections (11A, 11B) of the tissue bridge (10) accommodate adhesive layers (17A, 17B, 17C, 17D) for attaching the tissue bridge to a patient over a treatment area. The embodiment of FIG. 28 allows for each adhesive layer to have a variable degree of adhesion onto the tissue plane. For example, the outermost adhesive layers (17A,17D) may peel away from the tissue plane very easily while the inner sections of the adhesive layers (17B, 17C) require greater degrees of force to remove. Alternatively, the inner adhesive layers may be easily removable so that a partially attached tissue bridge can be repositioned prior to placing the lateral most sections onto a tissue plane. The lateral most sections in this embodiment could then be stronger and firmly affix the device only when the most effective position has been determined. Similarly, the tissue bridge (10) may direct larger forces of compression or distraction along the regions of the innermost layers (17B, 17C) and forces of lower magnitude along the outermost regions (17A, 17D).

Figure 29A:
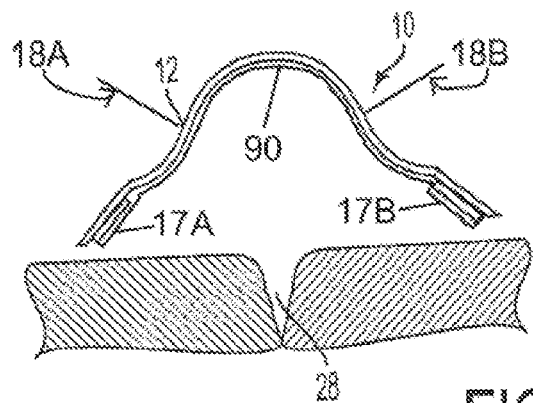
FIGS. 29A-29D illustrate a tissue bridge according to this disclosure and utilizing a tissue bridge in combination with a flexible sheet stretched for placement via tabs.
Figure 29B:
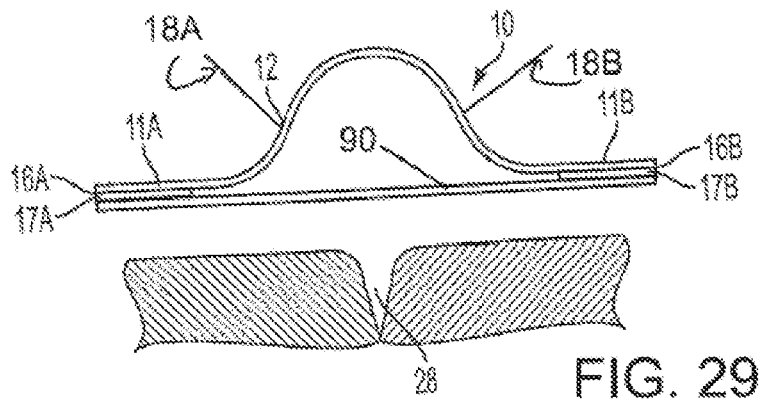
Figure 29C:
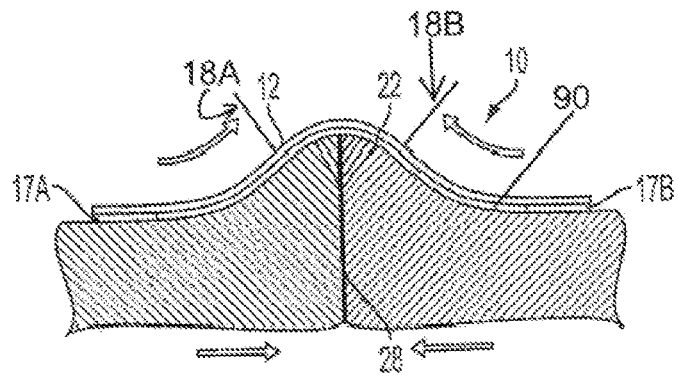
Figure 29D:
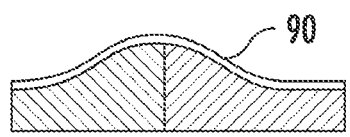

In a final set of figures illustrating the invention disclosed herein, the embodiment of FIG. 19H has been expanded to show an environmental use of the tissue bridge (10) having tabs or handles (18A, 18B) that can be manually pinched together to expand the tissue bridge (10). The tissue bridge (10) then expands the medicinal sheet (90) placed across a treatment area on a tissue plane (5). FIG. 29A shows the tissue bridge (10) in its at-rest state before deformation. FIG. 29B shows a pre-loaded tissue bridge according to this invention. In FIG. 29C, the tissue bridge and the medicinal sheet operate as a combination tissue bridge to evert the treatment area and reduce tension across the tissue plane in the region of the treatment area. In FIG. 29D, the tissue bridge (10) has been removed, leaving on the medicinal sheet and showing a lower level of eversion across the treatment area (28).

The tissue bridges disclosed herein may be made of numerous polymeric materials (e.g., plastics) that provide proper elasticity for pre-loading and releasing forces and sufficient rigidity to hold the device onto a tissue plane. Manufacturing systems common to these kinds of materials may be used to create the tissue bridges according to desired specifications. A single piece construction is useful for efficiently manufacturing the tissue bridges, but the device may incorporate multiple parts as necessary at the option of the user. The adhesives, adhesive sheets, and flexible sheets disclosed above are likewise commonly used by those of skill in the art of adhesives and polymeric sheets. The tissue bridges may be coated for medical purposes or patient comfort (e.g., a silicone coating reducing abrasions or friction from the tissue bridge and simultaneously incorporating a healing effect on a treatment area).

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A tissue bridge for directing forces onto a tissue plane, the tissue bridge comprising:
   a central section extending over an area, the central section comprising first and second sides and corresponding openings defined within the first and second sides, wherein the central section is flexible to allow the first and second sides to have (i) a predefined at-rest separation distance between the first and second sides and (ii) a distortion-induced separation distance between the first and second sides, and wherein the distortion-induced separation distance is larger than the at-rest separation distance;
   a first lateral section extending from the first side of the central section, wherein the first lateral section comprises an inner end section extending inwardly from the first side of the central section into the area over which the central section extends;
   a second lateral section extending from the second side of the central section, wherein the second lateral section comprises an inner end section extending inwardly from the second side of the central section into the area over which the central section extends; and respective attachment zones on the lateral sections configured to be connected to the tissue plane;
wherein the first lateral section and the second lateral section comprise corresponding openings.

2. The tissue bridge according to claim 1, wherein:
the first side of the central section is connected to the first lateral section at a first location that is positioned between, and distant from, opposite ends of the first lateral section; and
the second side of the central section is connected to the second lateral section at a second location that is positioned between, and distant from, opposite ends of the second lateral section.

3. The tissue bridge according to claim 2, wherein the connection between the first side of the central section and the first lateral section and the connection between the second side of the central section and the second lateral section both comprise a movable joint.

4. The tissue bridge according to claim 1, wherein:
the central section and the lateral sections comprise a single piece construction; and
the central section comprises a flexible arch.

5. The tissue bridge according to claim 1, wherein:
each of the first and second lateral sections includes an outer end section; and
the outer end sections extend outwardly, obliquely downwardly relative to an axis that both the predefined at-rest separation distance and the distortion-induced separation distance extend along, so that the outer end sections extend divergently away from one another.

6. The tissue bridge according to claim 1, wherein the attachment zones comprise adhesive tabs extending from the first and second lateral sections for attaching the tissue bridge to the tissue plane.

7. A system, comprising:
a tissue bridge for directing forces onto a tissue plane, the tissue bridge comprising:
a central section extending over an area, the central section comprising first and second sides and corresponding openings defined within the first and second sides, wherein the central section is flexible to allow the first and second sides to have (i) a predefined at-rest separation distance between the first and second sides and (ii) a distortion-induced separation distance between the first and second sides, and wherein the distortion-induced separation distance is larger than the at-rest separation distance;
a first lateral section extending from the first side of the central section, wherein the first lateral section comprises an inner end section extending inwardly from the first side of the central section into the area over which the central section extends;
a second lateral section extending from the second side of the central section, wherein the second lateral section comprises an inner end section extending inwardly from the second side of the central section into the area over which the central section extends; and
respective attachment zones on the lateral sections configured to be connected to the tissue plane; and
a hand-held deforming mechanism configured to distort the tissue bridge by:
applying a downward force to a central portion of the central section; and
applying upward forces to the tissue bridge at a first location and a second location, wherein the first location and second location are on opposite sides of the central portion of the central section.

8. The system according to claim 7, wherein:
the first side of the central section is connected to the first lateral section at a first connecting location that is positioned between, and distant from, opposite ends of the first lateral section; and
the second side of the central section is connected to the second lateral section at a second connecting location that is positioned between, and distant from, opposite ends of the second lateral section.

9. The system according to claim 7, wherein:
the central section and the lateral sections comprise a single piece construction; and
the central section comprises a flexible arch.

10. The system according to claim 7, wherein:
each of the first and second lateral sections includes an outer end section; and
the outer end sections extend outwardly, obliquely downwardly relative to an axis that both the predefined at-rest separation distance and the distortion-induced separation distance extend along, so that the outer end sections extend divergently away from one another.

11. The system according to claim 7, wherein the attachment zones comprise adhesive tabs extending from the first and second lateral sections for attaching the tissue bridge to the tissue plane.

12. The system according to claim 7, wherein the first lateral section and the second lateral section comprise corresponding openings.

13. The system according to claim 7, wherein the first location is on the first side of the central section and the second location is on the second side of the central section.

14. The system according to claim 7, wherein:
the tissue bridge comprises:
a first shoulder extending from the first side of the central section to the first lateral section; and
a second shoulder extending from the second side of the central section to the first lateral section; and
the first location is on the first shoulder and the second location is on the second shoulder.

15. The system according to claim 7, wherein the first location is on the first lateral section and the second location is on the second lateral section.

* * * * *